US012735741B2

(12) United States Patent
Batey et al.

(10) Patent No.: US 12,735,741 B2
(45) Date of Patent: Sep. 15, 2026

(54) COMPOSITIONS, METHODS AND USES FOR QUANTIFYING TRANSCRIPTION AND BIOSENSING OF SMALL MOLECULES USING A NOVEL TYPE VI CRISPR-CAS ASSAY

(71) Applicant: THE REGENTS OF THE UNIVERSITY OF COLORADO, Denver, CO (US)

(72) Inventors: Robert T. Batey, Boulder, CO (US); Roman S. Iwasaki Cordero, Boulder, CO (US)

(73) Assignee: The Regents of the University of Colorado, Denver, CO (US)

( * ) Notice: Subject to any disclaimer, the term of this patent is extended or adjusted under 35 U.S.C. 154(b) by 812 days.

(21) Appl. No.: 18/052,677

(22) Filed: Nov. 4, 2022

(65) Prior Publication Data

US 2023/0279482 A1 Sep. 7, 2023

Related U.S. Application Data

(63) Continuation of application No. PCT/US2021/031820, filed on May 11, 2021.

(Continued)

(51) Int. Cl.
*C12Q 1/6865* (2018.01)
*C12Q 1/6851* (2018.01)
*C12Q 1/6855* (2018.01)

(52) U.S. Cl.
CPC ......... *C12Q 1/6865* (2013.01); *C12Q 1/6851* (2013.01); *C12Q 1/6855* (2013.01)

(58) Field of Classification Search
CPC ......................... C12N 2310/20; C12Q 1/6825; C12Q 1/6897; C12Q 1/6865
See application file for complete search history.

(56) References Cited

U.S. PATENT DOCUMENTS

2018/0305773 A1* 10/2018 Abudayyeh .......... C12Q 1/6883
2019/0002875 A1 1/2019 Cheng et al.

FOREIGN PATENT DOCUMENTS

WO 2019071051 A1 4/2019

OTHER PUBLICATIONS

Burmistrz et al., "RNA-Targeting CRISPR-Cas Systems and Their Applications," International Journal of Molecular Sciences, vol. 21, pp. 2-14. (Year: 2020).*

(Continued)

*Primary Examiner* — Young J Kim
(74) *Attorney, Agent, or Firm* — Polsinelli PC

(57) ABSTRACT

Embodiments of the instant disclosure relate to novel compositions and methods for analyte detection by quantifying transcription of RNA using CRISPR-based approaches. In certain embodiments, constructs of use in assays disclosed herein can include a novel double-stranded DNA sequence having at least one transcriptional promoter, at least one regulatory element, and a target sequence. In some embodiments, constructs disclosed herein can be used in a system for quantifying transcriptional output in a sample in order to detect presence of an analyte. In other embodiments, constructs and systems disclosed herein can be used to measure enzyme activity, to detect and/or quantify at least one agent that modulates transcription, detect and/or quantify analytes (e.g. a contaminant, biomarkers or other agent) or a combination thereof in accordance with assessing health of a subject or assessing environmental conditions or contaminants.

14 Claims, 11 Drawing Sheets

Specification includes a Sequence Listing.

Related U.S. Application Data

(60) Provisional application No. 63/023,063, filed on May 11, 2020.

(56) References Cited

OTHER PUBLICATIONS

Marcano-Velazquez et al., "Developing Riboswitch-Mediated Gene Regulatory Controls in Thermophilic Bacteria," ACS Synthetic Biology, vol. 8, pp. 633-640. (Year: 2019).*

GenBank Accession No. ASL68970 [retrieved on-line, retrieval date Nov. 13, 2025; retrieved from: https://www.ncbi.nlm.nih.gov/protein/ASL68970] (Year: 2017).*

Shi, Y. et al., "Genetic Analysis of Riboswitch-mediated Transcriptional Regulation Responding to Mn2+ in *Salmonella*", Journal of Biological Chemistry, vol. 289, No. 16, Apr. 16, 2014, pp. 11353-11366.

Walter, T et al., "Point-of-Use Detection of Environmental Fluoride via a Cell-Free Riboswitch-Based Biosensor", ACS Synthetic Biology, vol. 9, No. 1, Jan. 17, 2020, pp. 10-18.

Alam, K. K., et al., "Rapid, Low-Cost Detection of Water Contaminants Using Regulated In Vitro Transcription", bioRxiv, May 2, 2019, pp. 1-38.

Gootenberg, J. S. et al., "Nucleic acid detection with CRISPR-Cas13a/C2c2", Science, vol. 356, No. 6336, Apr. 28, 2017 (Apr. 28, 2017), pp. 438-442.

Iwasaki, R. S. et al., "SPRINT: a Cas13a-based platform for detection of small molecules", Nucleic Acids Research, vol. 48, No. 17, Aug. 14, 2020, pp. 1-16.

Liang, M. et al., "A CRISPR-Cas 12a-derived biosensing platform for the highly sensitive detection of diverse small molecules", Nature Communications, vol. 10, No. 1, Aug. 14, 2019, pp. 1-9.

Xiong, Y. et al., "Functional DNA Regulated CRISPR-Cas12a Sensors for Point-of-Care Diagnostics of Non-Nucleic-Acid Targets", Journal of the American Chemical Society, vol. 142, No. 1, Jan. 8, 2020, pp. 207-213.

Zhan, H. et al., "Engineering Cellular Signal Sensors based on CRISPR-sgRNA Reconstruction Approaches", International Journal of Biological Sciences, vol. 16, No. 8, Feb. 21, 2020, pp. 1441-1449.

* cited by examiner

Tryptophan
Tryptamine
Lysine
5-Hydroxytryptophan (5-HTP)
5-Hydroxytryptamine (Serotonin)

SEQUENCE LISTING

```
Sequence total quantity: 45
SEQ ID NO: 1            moltype = DNA  length = 24
FEATURE                 Location/Qualifiers
misc_feature            1..24
                        note = Synthetic construct - primer
source                  1..24
                        mol_type = other DNA
                        organism = synthetic construct
SEQUENCE: 1
gctagccaca gctaacacca cgtc                                          24

SEQ ID NO: 2            moltype = DNA  length = 27
FEATURE                 Location/Qualifiers
misc_feature            1..27
                        note = Synthetic construct - primer
source                  1..27
                        mol_type = other DNA
                        organism = synthetic construct
SEQUENCE: 2
ctttatgctt ccggctcgta tgttgtg                                       27
```

-continued

```
SEQ ID NO: 3            moltype = DNA  length = 22
FEATURE                 Location/Qualifiers
misc_feature            1..22
                        note = Synthetic construct - primer
source                  1..22
                        mol_type = other DNA
                        organism = synthetic construct
SEQUENCE: 3
ctaaggatga tttctggaat tc                                              22

SEQ ID NO: 4            moltype = DNA  length = 31
FEATURE                 Location/Qualifiers
misc_feature            1..31
                        note = Synthetic construct - primer
source                  1..31
                        mol_type = other DNA
                        organism = synthetic construct
SEQUENCE: 4
atttatcaaa acatttaagt aaaggagttt g                                    31

SEQ ID NO: 5            moltype = DNA  length = 34
FEATURE                 Location/Qualifiers
misc_feature            1..34
                        note = Synthetic construct - primer
source                  1..34
                        mol_type = other DNA
                        organism = synthetic construct
SEQUENCE: 5
aatagctatt taatttgaat atattatacg agcc                                 34

SEQ ID NO: 6            moltype = DNA  length = 15
FEATURE                 Location/Qualifiers
misc_feature            1..15
                        note = Synthetic construct - primer
source                  1..15
                        mol_type = other DNA
                        organism = synthetic construct
SEQUENCE: 6
cgcttctgcg ttctg                                                      15

SEQ ID NO: 7            moltype = DNA  length = 20
FEATURE                 Location/Qualifiers
misc_feature            1..20
                        note = Synthetic construct - primer
source                  1..20
                        mol_type = other DNA
                        organism = synthetic construct
SEQUENCE: 7
ggccagtgaa ttcgagctcg                                                 20

SEQ ID NO: 8            moltype = DNA  length = 27
FEATURE                 Location/Qualifiers
misc_feature            1..27
                        note = Synthetic construct - primer
source                  1..27
                        mol_type = other DNA
                        organism = synthetic construct
SEQUENCE: 8
gaatatatta tacgagcctt atgcatg                                         27

SEQ ID NO: 9            moltype = DNA  length = 23
FEATURE                 Location/Qualifiers
misc_feature            1..23
                        note = Synthetic construct - primer
source                  1..23
                        mol_type = other DNA
                        organism = synthetic construct
SEQUENCE: 9
gaagcttggg cccgaacaaa aac                                             23

SEQ ID NO: 10           moltype = DNA  length = 26
FEATURE                 Location/Qualifiers
misc_feature            1..26
                        note = Synthetic construct - primer
source                  1..26
                        mol_type = other DNA
                        organism = synthetic construct
SEQUENCE: 10
```

-continued

```
agatctttag aattccagaa atcatc                                   26

SEQ ID NO: 11          moltype = DNA  length = 31
FEATURE                Location/Qualifiers
misc_feature           1..31
                       note = Synthetic construct - primer
source                 1..31
                       mol_type = other DNA
                       organism = synthetic construct
SEQUENCE: 11
gatcctctag aaatatggat tacttggtag g                             31

SEQ ID NO: 12          moltype = DNA  length = 30
FEATURE                Location/Qualifiers
misc_feature           1..30
                       note = Synthetic construct - primer
source                 1..30
                       mol_type = other DNA
                       organism = synthetic construct
SEQUENCE: 12
ggcggcgaat tctaatacga ctcactatag                               30

SEQ ID NO: 13          moltype = DNA  length = 60
FEATURE                Location/Qualifiers
misc_feature           1..60
                       note = Synthetic construct - primer
source                 1..60
                       mol_type = other DNA
                       organism = synthetic construct
SEQUENCE: 13
gcataaggct cgtataatat attccaaaaa attaataaca ttttctctta tcgagagttg  60

SEQ ID NO: 14          moltype = DNA  length = 37
FEATURE                Location/Qualifiers
misc_feature           1..37
                       note = Synthetic construct - primer
source                 1..37
                       mol_type = other DNA
                       organism = synthetic construct
SEQUENCE: 14
ctcatgggaa agaggctttt tggccagtga attcgag                       37

SEQ ID NO: 15          moltype = DNA  length = 35
FEATURE                Location/Qualifiers
misc_feature           1..35
                       note = Synthetic construct - tac promoter
source                 1..35
                       mol_type = other DNA
                       organism = synthetic construct
SEQUENCE: 15
ttgacaggca tgcataaggc tcgtataata tattc                         35

SEQ ID NO: 16          moltype = DNA  length = 19
FEATURE                Location/Qualifiers
misc_feature           1..19
                       note = Synthetic construct - T7 promoter
source                 1..19
                       mol_type = other DNA
                       organism = synthetic construct
SEQUENCE: 16
taatacgact cactatagg                                           19

SEQ ID NO: 17          moltype = DNA  length = 30
FEATURE                Location/Qualifiers
misc_feature           1..30
                       note = Synthetic construct - Cas13a target site
source                 1..30
                       mol_type = other DNA
                       organism = synthetic construct
SEQUENCE: 17
gatcctctag aaatatggat tacttggtag                               30

SEQ ID NO: 18          moltype = DNA  length = 66
FEATURE                Location/Qualifiers
misc_feature           1..66
                       note = Synthetic construct - crRNA
source                 1..66
                       mol_type = other DNA
                       organism = synthetic construct
```

-continued

```
SEQUENCE: 18
gatttagact accccaaaaa cgaaggggac taaaacctac caagtaatcc atatttctag  60
aggatc                                                             66

SEQ ID NO: 19          moltype = DNA  length = 180
FEATURE                Location/Qualifiers
misc_feature           1..180
                       note = Synthetic construct - guanine riboswitch
source                 1..180
                       mol_type = other DNA
                       organism = synthetic construct
SEQUENCE: 19
aattaaatag ctattatcac gatttttata atcgcgtgga tatggcacgc aagtttctac  60
cgggcaccgt aaatgtccga ctaaaaatcc tgattacaaa atttgtttat gacatttttt  120
gtaatcagga tttttttattt atcaaaacat ttaagtaaag gagtttgtta tgtttttttt  180

SEQ ID NO: 20          moltype = DNA  length = 57
FEATURE                Location/Qualifiers
misc_feature           1..57
                       note = Synthetic construct - guanine aptamer
source                 1..57
                       mol_type = other DNA
                       organism = synthetic construct
SEQUENCE: 20
tataatcgcg tggatatggc acgcaagttt ctaccgggca ccgtaaatgt ccgacta     57

SEQ ID NO: 21          moltype = DNA  length = 253
FEATURE                Location/Qualifiers
misc_feature           1..253
                       note = Synthetic construct - FMN riboswitch
source                 1..253
                       mol_type = other DNA
                       organism = synthetic construct
SEQUENCE: 21
aattaaatag ctattatcac gattttcgg ggcagggtgg aaatcccgac cggcggtagt  60
aaagcacatt tgctttagag cccgtgaccc gtgtgcataa gcacgcggtg gattcagttt  120
aagctgaagc cgacagtgaa agtctggatg ggagaaaaat cctgattaca aaatttgttt  180
atgacatttt ttgtaatcag gattttttta tttatcaaaa catttaagta aaggagtttg  240
ttatgttttt ttt                                                     253

SEQ ID NO: 22          moltype = DNA  length = 127
FEATURE                Location/Qualifiers
misc_feature           1..127
                       note = Synthetic construct - FMN aptamer
source                 1..127
                       mol_type = other DNA
                       organism = synthetic construct
SEQUENCE: 22
cggggcaggg tggaaatccc gaccggcggt agtaaagcac atttgcttta gagcccgtga  60
cccgtgtgca taagcacgcg gtggattcag tttaagctga agccgacagt gaaagtctgg  120
atgggag                                                            127

SEQ ID NO: 23          moltype = DNA  length = 231
FEATURE                Location/Qualifiers
misc_feature           1..231
                       note = Synthetic construct - SAM riboswitch
source                 1..231
                       mol_type = other DNA
                       organism = synthetic construct
SEQUENCE: 23
aattaaatag ctattatcac gattttatca agagaagcag agggactggc ccgacgaagc  60
ttcagcaacc ggtgtaatgg cgatcagcca tgaccaaggt gctaaatcca gcaagctcga  120
acagcttgga agataaaatc ctgattacaa aatttgttta tgacattttt tgtaatcagg  180
atttttttatt tatcaaaaca tttaagtaaa ggagtttgtt atgttttttt t          231

SEQ ID NO: 24          moltype = DNA  length = 108
FEATURE                Location/Qualifiers
misc_feature           1..108
                       note = Synthetic construct - SAM aptamer
source                 1..108
                       mol_type = other DNA
                       organism = synthetic construct
SEQUENCE: 24
atcaagagaa gcagagggac tggcccgacg aagcttcagc aaccggtgta atggcgatca  60
gccatgacca aggtgctaaa tccagcaagc tcgaacagct tggaagat               108

SEQ ID NO: 25          moltype = DNA  length = 100
FEATURE                Location/Qualifiers
misc_feature           1..100
```

-continued

```
                      note = Synthetic construct - adenine riboswitch
source                1..100
                      mol_type = other DNA
                      organism = synthetic construct
SEQUENCE: 25
cacttgtata acctcaataa tatggtttga gggtgtctac caggaaccgt aaaatcctga  60
ttacaagccg ttttttcggc ttgtaatcag gatttttttt                        100

SEQ ID NO: 26         moltype = DNA  length = 57
FEATURE               Location/Qualifiers
misc_feature          1..57
                      note = Synthetic construct - adenine aptamer
source                1..57
                      mol_type = other DNA
                      organism = synthetic construct
SEQUENCE: 26
tataacctca ataatatggt ttgagggtgt ctaccaggaa ccgtaaaatc ctgatta     57

SEQ ID NO: 27         moltype = DNA  length = 79
FEATURE               Location/Qualifiers
misc_feature          1..79
                      note = Synthetic construct - fluoride riboswitch
source                1..79
                      mol_type = other DNA
                      organism = synthetic construct
SEQUENCE: 27
taggcgatgg agttcgccat aaacgctgct tagctaatga ctcctaccag tatcactact  60
ggtaggagtc tatttttttt                                              79

SEQ ID NO: 28         moltype = DNA  length = 229
FEATURE               Location/Qualifiers
misc_feature          1..229
                      note = Synthetic construct - SAM riboswitch
source                1..229
                      mol_type = other DNA
                      organism = synthetic construct
SEQUENCE: 28
caaaaaatta ataacatttt ctcttatcga gagttgggcg agggattggc cttttgaccc  60
caacagcaac cgaccgtaat accattgtga aatggggcgc actgcttttc gcgccgagac  120
tgatgtctca taaggcacgg tgctaattcc atcagattgt gtctgagaga tgagagaggc  180
agtgttttac gtagaaaagc ctctttctct catgggaaag aggctttttt              229

SEQ ID NO: 29         moltype = DNA  length = 22
FEATURE               Location/Qualifiers
misc_feature          1..22
                      note = Synthetic construct - zinc aTF operator
source                1..22
                      mol_type = other DNA
                      organism = synthetic construct
SEQUENCE: 29
cacatgaaca gttattcaga ta                                           22

SEQ ID NO: 30         moltype = DNA  length = 19
FEATURE               Location/Qualifiers
misc_feature          1..19
                      note = Synthetic construct - tetracycline aTF operator
source                1..19
                      mol_type = other DNA
                      organism = synthetic construct
SEQUENCE: 30
tccctatcag tgatagaga                                               19

SEQ ID NO: 31         moltype = DNA  length = 104
FEATURE               Location/Qualifiers
misc_feature          1..104
                      note = Synthetic construct
source                1..104
                      mol_type = other DNA
                      organism = synthetic construct
SEQUENCE: 31
gctagccaca gctaacacca cgtcgtccct atctgctgcc ctaggtctat gagtggttgc  60
tggataactt gacaggcatg cataaggctc gtataatata ttca                   104

SEQ ID NO: 32         moltype = DNA  length = 52
FEATURE               Location/Qualifiers
misc_feature          1..52
                      note = Synthetic construct
source                1..52
                      mol_type = other DNA
```

```
                        organism = synthetic construct
SEQUENCE: 32
ctaaggatga tttctggaat tctaaagatc ttaatacgac tcactatagg ga         52

SEQ ID NO: 33           moltype = DNA  length = 173
FEATURE                 Location/Qualifiers
misc_feature            1..173
                        note = Synthetic construct
source                  1..173
                        mol_type = other DNA
                        organism = synthetic construct
SEQUENCE: 33
ggccagtgaa ttcgagctcg gtacccgggg atcctctaga aatatggatt acttggtaga  60
acagcaatct actcgacctg caggcatgca agcttggcgt aatcatggtc atagctgttt  120
cctgtgttta tccgctcaca attccacaca acatacgagc cggaagcata aag        173

SEQ ID NO: 34           moltype = DNA  length = 2905
FEATURE                 Location/Qualifiers
misc_feature            1..2905
                        note = Synthetic construct - plasmid
source                  1..2905
                        mol_type = other DNA
                        organism = synthetic construct
SEQUENCE: 34
gcgagttaca tgatccccca tgttgtgcaa aaaagcggtt agctccttcg gtcctccgat  60
cgttgtcaga agtaagttgg ccgcagtgtt atcactcatg gttatggcag cactgcataa  120
ttctcttact gtcatgccat ccgtaagatg cttttctgtg actggtgagt actcaaccaa  180
gtcattctga gaatagtgta tgcggcgacc gagttgctct tgcccggcgt caatacggga  240
taataccgcg ccacatagca gaactttaaa agtgctcatc attggaaaac gttcttcggg  300
gcgaaaactc tcaaggatct taccgctgtt gagatccagt tcgatgtaac ccactcgtgc  360
acccaactga tcttcagcat cttttacttt caccagcgtt tctgggtgag caaaaacagg  420
aaggcaaaat gccgcaaaaa agggaataag ggcgacacgg aaatgttgaa tactcatact  480
cttccttttt caatattatt gaagcattta tcagggttat tgtctcatga gcggatacat  540
atttgaatgt atttagaaaa ataaacaaat aggggttccg cgcacatttc cccgaaaagt  600
gccacctgac gtctaagaaa ccattattat catgacatta acctataaaa ataggcgtat  660
cacgaggcag aatttcagat aaaaaaaatc cttagctttc gctaaggatg atttctggaa  720
ttctaaagat ctgcgctagc cacagctaac accacgtcgt ccctatctgc tgccctaggt  780
ctatgagtgg ttgctggata acttgacagg catgcataag gctcgtataa tatattcaaa  840
ttaaatagct attatcacga tttttataat cgcgtggata tggcacgcaa gtttctaccg  900
ggcaccgtaa atgtccgact aaaaatcctg attacaaaat ttgtttatga cattttttgt  960
aatcaggatt ttttatttat caaaacattt aagtaaagga gtttgttatg ttttttttgg  1020
ccagtgaatt cgagctcggt acccggggat cctctagaaa tatggattac ttggtagaac  1080
agcaatctac tcgacctgca ggcatgcaag cttggcgtaa tcatggtcat agctgtttcc  1140
tgtgtttatc cgctcacaat tccacacaac atacgagccg gaagcataaa ggaagcttgg  1200
gcccgaacaa aaactcatct cagaagagga tctgaatagc gccgtcgacc atcatcatca  1260
tcatcattga gtttaaacgg tctccagctt ggctgttttg gcggatgaga gaagattttc  1320
agcctgatac agattaaatc agaacgcaga agcggtctga taaaacagaa tttgcctggc  1380
ggcagtagcg cggtggtccc acctgacccc atgccgaact cagaagtgaa acgccgtagc  1440
gccgatggta gtgtggggtc tccccatgcg agagtaggga actgccaggc atcaaataaa  1500
acgaaaggct cagtcgaaag actgggcctt tcgttttatc tgttgtttgt cggtgaactg  1560
gatccttact cgagtctaga ctgcaggctt cctcgctcac tgactcgctg cgctcggtcg  1620
ttcggctgcg gcgagcggta tcagctcact caaaggcggt aatacggtta tccacagaat  1680
caggggataa cgcaggaaag aacatgtgag caaaaggcca gcaaaaggcc aggaaccgta  1740
aaaaggccgc gttgctggcg tttttccata ggctccgccc ccctgacgag catcacaaaa  1800
atcgacgctc aagtcagagg tggcgaaacc cgacaggact ataaagatac caggcgtttc  1860
cccctggaag ctccctcgtg cgctctcctg ttccgaccct gccgcttacc ggatacctgt  1920
ccgcctttct cccttcggga agcgtggcgc tttctcatag ctcacgctgt aggtatctca  1980
gttcggtgta ggtcgttcgc tccaagctgg gctgtgtgca cgaacccccc gttcagcccg  2040
accgctgcgc cttatccggt aactatcgtc ttgagtccaa cccggtaaga cacgacttat  2100
cgccactggc agcagccact ggtaacagga ttagcagagc gaggtatgta ggcggtgcta  2160
cagagttctt gaagtggtgg cctaactacg gctacactag aaggacagta tttggtatct  2220
gcgctctgct gaagccagtt accttcggaa aaagagttgg tagctcttga tccggcaaac  2280
aaaccaccgc tggtagcggt ggtttttttg tttgcaagca gcagattacg cgcagaaaaa  2340
aaggatctca agaagatcct ttgatctttt ctacggggtc tgacgctcag tggaacgaaa  2400
actcacgtta agggattttg gtcatgagat tatcaaaaag gatcttcacc tagatccttt  2460
taaattaaaa atgaagtttt aaatcaatct aaagtatata tgagtaaact tggtctgaca  2520
gttaccaatg cttaatcagt gaggcaccta tctcagcgat ctgtctattt cgttcatcca  2580
tagttgcctg actccccgtc gtgtagataa ctacgatacg ggagggctta ccatctggcc  2640
ccagtgctgc aatgataccg cgagacccac gctcaccggc tccagattta tcagcaataa  2700
accagccagc cggaagggcc gagcgcagaa gtggtcctgc aactttatcc gcctccatcc  2760
agtctattaa ttgttgccgg gaagctagag taagtagttc gccagttaat agtttgcgca  2820
acgttgttgc cattgctaca ggcatcgtgg tgtcacgctc gtcgtttggt atggcttcat  2880
tcagctccgg ttcccaacga tcaag                                       2905

SEQ ID NO: 35           moltype = DNA  length = 101
FEATURE                 Location/Qualifiers
misc_feature            1..101
                        note = Synthetic construct
source                  1..101
```

```
                         mol_type = other DNA
                         organism = synthetic construct
SEQUENCE: 35
ggcggcgaat tctaatacga ctcactatag ggaagattt agactacccc aaaaacgaag  60
gggactaaaa cctaccaagt aatccatatt tctagaggat c                     101

SEQ ID NO: 36            moltype = DNA  length = 276
FEATURE                  Location/Qualifiers
misc_feature             1..276
                         note = Synthetic construct
source                   1..276
                         mol_type = other DNA
                         organism = synthetic construct
SEQUENCE: 36
gctagccaca gctaacacca cgtcgtccct atctgctgcc ctaggtctat gagtggttgc  60
tggataactt gacaggcatg cataaggctc gtataatata ttcggccagt gaattcgagc  120
tcggtacccg gggatcctct agaaatatgg attacttggt agaacagcaa tctactcgac  180
ctgcaggcat gcaagcttgg cgtaatcatg gtcatagctg tttcctgtgt ttatccgctc  240
acaattccac acaacatacg agccggaagc ataaag                           276

SEQ ID NO: 37            moltype = DNA  length = 457
FEATURE                  Location/Qualifiers
misc_feature             1..457
                         note = Synthetic construct
source                   1..457
                         mol_type = other DNA
                         organism = synthetic construct
SEQUENCE: 37
gctagccaca gctaacacca cgtcgtccct atctgctgcc ctaggtctat gagtggttgc  60
tggataactt gacaggcatg cataaggctc gtataatata ttcaaattaa atagctatta  120
tcacgatttt tataatcgcg tggatatggc acgcaagttt ctaccgggca ccgtaaatgt  180
ccgactaaaa atcctgatta caaaatttgt ttatgacatt ttttgtaatc aggatttttt  240
atttatcaaa acatttaagt aaaggagttt gttatgtttt ttttggccag tgaattcgag  300
ctcggtaccc ggggatcctc tagaaatatg gattacttgg tagaacagca atctactcga  360
cctgcaggca tgcaagcttg gcgtaatcat ggtcatagct gtttcctgtg tttatccgct  420
cacaattcca cacaacatac gagccggaag cataaag                          457

SEQ ID NO: 38            moltype = DNA  length = 530
FEATURE                  Location/Qualifiers
misc_feature             1..530
                         note = Synthetic construct
source                   1..530
                         mol_type = other DNA
                         organism = synthetic construct
SEQUENCE: 38
gctagccaca gctaacacca cgtcgtccct atctgctgcc ctaggtctat gagtggttgc  60
tggataactt gacaggcatg cataaggctc gtataatata ttcaaattaa atagctatta  120
tcacgatttt tcggggcagg gtggaaatcc cgaccggcgg tagtaaagca catttgcttt  180
agagcccgtg acccgtgtgc ataagcacgc ggtggattca gtttaagctg aagccgacag  240
tgaaagtctg gatgggagaa aaatcctgat tacaaaattt gtttatgaca ttttttgtaa  300
tcaggatttt tttatttatc aaaacattta agtaaaggag tttgttatgt ttttttggc  360
cagtgaattc gagctcggta cccggggatc ctctagaaat atggattact tggtagaaca  420
gcaatctact cgacctgcag gcatgcaagc ttggcgtaat catggtcata gctgtttcct  480
gtgtttatcc gctcacaatt ccacacaaca tacgagccgg aagcataaag             530

SEQ ID NO: 39            moltype = DNA  length = 508
FEATURE                  Location/Qualifiers
misc_feature             1..508
                         note = Synthetic construct
source                   1..508
                         mol_type = other DNA
                         organism = synthetic construct
SEQUENCE: 39
gctagccaca gctaacacca cgtcgtccct atctgctgcc ctaggtctat gagtggttgc  60
tggataactt gacaggcatg cataaggctc gtataatata ttcaaattaa atagctatta  120
tcacgatttt atcaagagaa gcagagggac tggcccgacg aagcttcagc aaccggtgta  180
atggcgatca gccatgacca aggtgctaaa tccagcaagc tcgaacagct tggaagataa  240
aatcctgatt acaaaatttg tttatgacat tttttgtaat caggattttt tatttatcaa  300
aacatttaag taaaggagtt tgttatgttt tttttggcca gtgaattcga gctcggtacc  360
cggggatcct ctagaaatat ggattacttg gtagaacagc aatctactcg acctgcaggc  420
atgcaagctt ggcgtaatca tggtcatagc tgtttcctgt gtttatccgc tcacaattcc  480
acacaacata cgagccggaa gcataaag                                    508

SEQ ID NO: 40            moltype = DNA  length = 377
FEATURE                  Location/Qualifiers
misc_feature             1..377
                         note = Synthetic construct
source                   1..377
                         mol_type = other DNA
```

-continued

```
                         organism = synthetic construct
SEQUENCE: 40
gctagccaca gctaacacca cgtcgtccct atctgctgcc ctaggtctat gagtggttgc  60
tggataactt gacaggcatg cataaggctc gtataatata ttcacacttg tataacctca  120
ataatatggt ttgagggtgt ctaccaggaa ccgtaaaatc ctgattacaa gccgtttttt  180
cggcttgtaa tcaggatttt ttttggccag tgaattcgag ctcggtaccc ggggatcctc  240
tagaaatatg gattacttgg tagaacagca atctactcga cctgcaggca tgcaagcttg  300
gcgtaatcat ggtcatagct gtttcctgtg tttatccgct cacaattcca cacaacatac  360
gagccggaag cataaag                                                 377

SEQ ID NO: 41            moltype = DNA  length = 355
FEATURE                  Location/Qualifiers
misc_feature             1..355
                         note = Synthetic construct
source                   1..355
                         mol_type = other DNA
                         organism = synthetic construct
SEQUENCE: 41
gctagccaca gctaacacca cgtcgtccct atctgctgcc ctaggtctat gagtggttgc  60
tggataactt gacaggcatg cataaggctc gtataatata ttctaggcga tggagttcgc  120
cataaacgct gcttagctaa tgactcctac cagtatcact actggtagga gtctattttt  180
ttggccagtg aattcgagct cggtacccgg ggatcctcta gaaatatgga ttacttggta  240
gaacagcaat ctactcgacc tgcaggcatg caagcttggc gtaatcatgg tcatagctgt  300
ttcctgtgtt tatccgctca caattccaca caacatacga gccggaagca taaag       355

SEQ ID NO: 42            moltype = DNA  length = 505
FEATURE                  Location/Qualifiers
misc_feature             1..505
                         note = Synthetic construct
source                   1..505
                         mol_type = other DNA
                         organism = synthetic construct
SEQUENCE: 42
gctagccaca gctaacacca cgtcgtccct atctgctgcc ctaggtctat gagtggttgc  60
tggataactt gacaggcatg cataaggctc gtataatata ttccaaaaaa ttaataacat  120
tttctcttat cgagagttgg gcgagggatt ggccttttga ccccaacagc aaccgaccgt  180
aataccattg tgaaatgggg cgcactgctt ttcgcgccga gactgatgtc tcataaggca  240
cggtgctaat tccatcagat tgtgtctgag agatgagaga ggcagtgttt tacgtagaaa  300
agcctctttc tctcatggga aagaggcttt ttggccagtg aattcgagct cggtacccgg  360
ggatcctcta gaaatatgga ttacttggta gaacagcaat ctactcgacc tgcaggcatg  420
caagcttggc gtaatcatgg tcatagctgt ttcctgtgtt tatccgctca caattccaca  480
caacatacga gccggaagca taaag                                        505

SEQ ID NO: 43            moltype = DNA  length = 223
FEATURE                  Location/Qualifiers
misc_feature             1..223
                         note = Synthetic construct
source                   1..223
                         mol_type = other DNA
                         organism = synthetic construct
SEQUENCE: 43
ctaaggatga tttctggaat tctaaagatc ttaatacgac tcactatagg ggccagtgaa  60
ttcgagctcg gtacccgggg atcctctaga aatatggatt acttggtaga acagcaatct  120
actcgacctg caggcatgca agcttggcgt aatcatggtc atagctgttt cctgtgttta  180
tccgctcaca attccacaca acatacgagc cggaagcata aag                    223

SEQ ID NO: 44            moltype = DNA  length = 247
FEATURE                  Location/Qualifiers
misc_feature             1..247
                         note = Synthetic construct
source                   1..247
                         mol_type = other DNA
                         organism = synthetic construct
SEQUENCE: 44
ctaaggatga tttctggaat tctaaagatc ttaatacgac tcactatagg gacacatgaa  60
cagttattca gataggccag tgaattcgag ctcggtaccc ggggatcctc tagaaatatg  120
gattacttgg tagaacagca atctactcga cctgcaggca tgcaagcttg gcgtaatcat  180
ggtcatagct gtttcctgtg tttatccgct cacaattcca cacaacatac gagccggaag  240
cataaag                                                            247

SEQ ID NO: 45            moltype = DNA  length = 244
FEATURE                  Location/Qualifiers
misc_feature             1..244
                         note = Synthetic construct
source                   1..244
                         mol_type = other DNA
                         organism = synthetic construct
SEQUENCE: 45
ctaaggatga tttctggaat tctaaagatc ttaatacgac tcactatagg gatccctatc  60
```

-continued

```
agtgatagag aggccagtga attcgagctc ggtacccggg gatcctctag aaatatggat  120
tacttggtag aacagcaatc tactcgacct gcaggcatgc aagcttggcg taatcatggt  180
catagctgtt tcctgtgttt atccgctcac aattccacac aacatacgag ccggaagcat  240
aaag                                                                244
```

COMPOSITIONS, METHODS AND USES FOR QUANTIFYING TRANSCRIPTION AND BIOSENSING OF SMALL MOLECULES USING A NOVEL TYPE VI CRISPR-CAS ASSAY

PRIORITY

This application is a continuation of PCT Application No. PCT/US2021/031820 filed May 11, 2021, which claims priority to U.S. Provisional Application No. 63/023,063 filed May 11, 2020, each of which is incorporated herein by reference in its entirety for all purposes.

STATEMENT REGARDING SEQUENCE LISTING

The instant application contains a Sequence Listing which is being submitted via ASCII copy, which was originally created on May 11, 2021, and has been updated to the new USPTO format on Nov. 4, 2022, now referred to as '101877-743452_CU5268BUS1', of 69 KB in size and having 45 sequences, which is incorporated herein by reference in its entirety for all purposes.

FIELD

Embodiments of the instant disclosure relate to compositions and methods for analyte detection by quantifying transcription of RNA using CRISPR-based approaches. In some embodiments, compositions and methods for quantification of RNA transcription can include an in vitro coupled or combination assay. In certain embodiments, constructs of use in assays disclosed herein can include novel double-stranded DNA sequence having at least one transcriptional promoter, at least one regulatory element, and encoding a unique target sequence. In some embodiments, assays disclosed herein can further include at least one other construct including, at least one "signal polynucleotide", one guide RNA polynucleotide (e.g. crRNA), one type VI CRISPR-Cas effector protein capable of binding to crRNA polynucleotide, one RNA polymerase, and a novel double-stranded DNA sequence. In some embodiments, a "signal polynucleotide" can be a "signal RNA." In some embodiments, constructs disclosed herein can be used in a system for quantifying transcriptional output in a sample. In other embodiments, constructs disclosed herein can be used to measure enzyme activity, to detect and/or quantify at least one agent that modulates transcription, detect and/or quantify presence of analytes (e.g. a contaminant or other agent) or a combination thereof. In certain embodiments, a type VI CRISPR-Cas effector protein can be a Cas13 orthologue.

BACKGROUND

Bacterial transcription is regulated by a myriad of different mechanisms that sense small molecules and other stimuli. Such mechanisms include riboswitches and allosteric transcription factors (aTF). Allosteric transcription factors can alter their binding affinity for a DNA site upon ligand binding. When the aptamer domain of a riboswitch specifically binds its cognate ligand, formation of alternative secondary RNA structures occurs in the downstream expression platform. While aTFs and riboswitches are capable of recognizing an array of compounds as inputs, transducing this into a robust and easily obtained output has been challenging. Therefore, there is a need for reliable systems for sensing and quantification of aptamer-ligand binding or aptamer-regulated transcription. In addition, there is a need for reliable systems for quantification that are easily adaptable to the detection of diverse classes of transcription-regulating compounds in a rapid, high-throughput manner.

SUMMARY

Embodiments of the instant disclosure relate to compositions, methods and systems for quantification of RNA transcription using CRISPR-based assay approaches. In certain embodiments, systems for quantifying transcriptional output in a sample using a rapid, reliable and repeatable assay methods are disclosed. In some embodiments, compositions and methods disclosed herein can be comparable to detection and quantification of transcription by state-of-the-art radiolabeling assays without the use of radiolabel. In other embodiments, compositions and methods disclosed herein can be an improvement over radiolabeling quantification-based methods due to increased speed, increased efficiency, ease of use, improved safety for testing and increased throughput of transcription assays. In other embodiments, compositions, methods and systems disclosed herein can provide for efficient combinations of small-molecule dependent transcriptional regulation and CRISPR-mediated RNA cleavage assays into a single efficient reaction system.

In accordance with these embodiments, systems can include at least one type VI CRISPR-Cas effector protein; at least one CRISPR RNA (crRNA); at least one novel double-stranded DNA sequence, at least one fluorescently labeled RNA oligonucleotide having a non-target sequence; and at least one RNA polymerase. In accordance with these embodiments, the novel double-stranded DNA sequence includes, but is not limited to, a transcriptional promoter, at least one regulatory element and a unique target polynucleotide sequence. In some embodiments, assays disclosed herein can further include at least a second polynucleotide including, at least one "signal polynucleotide" that can be labeled or associate with a fluorophore and a quencher, one guide RNA polynucleotide (e.g. crRNA), one type VI CRISPR-Cas effector protein that is capable of hybridizing with the crRNA polynucleotide, one RNA polymerase, and a novel double-stranded DNA sequence. In some embodiments, constructs disclosed herein can be used in systems for quantifying transcriptional output in a sample. In certain embodiments, novel double-stranded DNA sequences can be transcribed via the RNA polymerase, signifying that the RNA transcript contains an RNA target sequence when the transcription process is elongated sufficiently to include the target sequence. In certain embodiments, a target sequence is a polynucleotide of about 10 to about 500 nucleotides in length. In accordance with these embodiments, a target polynucleotide is embedded within the transcribed RNA. In other embodiments, the target sequence is complementary to CRISPR RNA bound to the Cas protein. In some embodiments, CRISPR-Cas effectors that bind to a crRNA polynucleotide can be guided to a RNA target sequence on a RNA transcript. In some embodiments, hybridization of a CRISPR-Cas Effector/guide RNA complex disclosed herein to a target RNA transcript can cause the CRISPR-Cas Effector/guide RNA to degrade the "signal polynucleotide" which can de-quench fluorescence of one or more fluorophores associated with a "signal polynucleotide" creating a detectable signal. In further accordance with these embodiments, a type VI CRISPR-Cas effector protein herein can exhibit collateral RNase activity and/or can cleave a non-target sequence of a fluorescently-labeled RNA oligonucleotide after the type VI CRISPR-Cas effector protein herein forms a complex with a crRNA. In some embodiments, a non-target sequence can be a polynucleotide that is not complementary to the CRISPR RNA bound to the Cas protein. In certain embodiments, the signal can be detectable by the human eye, by instrumentation capable of detecting the signal, or combination thereof for more rapid detection of a signal. In some embodiments, constructs and systems disclosed herein can be used to quantify enzyme activity, to detect levels of one or more compounds that regulate (e.g. inhibits, stabilizes, induces and/or otherwise effects) transcription, or a combination thereof. In certain embodiments, a type VI CRISPR-Cas effector protein can be a Cas13 orthologue or similar. In other embodiments, a novel double-stranded DNA sequence herein can further include at least one riboswitch sequence, at least one allosteric transcription factor (aTF) operator sequence, or a combination thereof.

In certain embodiments, constructs of use in systems and methods disclosed herein are contemplated. In accordance with these embodiments, assays disclosed herein can include at least one type VI CRISPR-Cas effector protein; at least one guide RNA polynucleotide (crRNA) capable of binding a type VI CRISPR-Cas effector protein; at least one novel double-stranded DNA sequence that can include, but is not limited to, a transcriptional promoter, at least one regulatory element, a target sequence, or any combination thereof; and/or at least one fluorescently labeled RNA oligonucleotide (signal polynucleotide) that can include a non-target sequence. In some embodiments, at least one regulatory element disclosed herein can regulate downstream transcription of one or more target sequences. In accordance with these embodiments, a type VI CRISPR-Cas effector protein of the system herein can display collateral RNase activity and/or can cleave a non-target sequence of a fluorescently labeled RNA oligonucleotide after the type VI CRISPR-Cas effector protein is activated by the one or more target RNA sequence wherein released fluorescence can be detected. In some embodiments, at least one type VI CRISPR-Cas effector protein can be a Cas13 orthologue.

In other embodiments, compositions disclosed herein can be used in methods for quantifying transcriptional output in samples wherein the methods include contacting one or more samples with the following: reagents for transcribing the target sequence (e.g. target polynucleotide of interest); at least one type VI CRISPR-Cas effector protein; at least one guide RNA polynucleotide (crRNA) that is capable of binding a type VI CRISPR-Cas effector protein; at least one fluorescently labeled RNA oligonucleotide that includes a non-target sequence (e.g. "signal RNA"); at least one novel double-stranded DNA template including, but not limited to, a transcriptional promoter, at least one regulatory element, and/or a target polynucleotide sequence; and at least one RNA polymerase. In accordance with these embodiments, the at least one type VI CRISPR-Cas effector protein herein can have collateral RNase activity and can cleave a non-target sequence of a fluorescently labeled RNA oligonucleotide after the type VI CRISPR-Cas effector protein is activated by the target RNA sequence, producing a detectable signal. In accordance with these embodiments, a detectable signal from cleavage of the non-target sequence herein can be measured for presence and/or intensity, by observation by a health provider's or observer's eye for detecting transcriptional output in the sample with accuracy and improved turnaround time compared to other methods known in the art.

In some embodiments, kits are contemplated of use to store or transport constructs and systems disclosed herein for portable use. In accordance with these embodiments, kits contemplated herein can address a need for point-of-care or field-testing diagnostic or assessment devices. In some embodiments, kits herein can contain one or more composition, agent or component needed to convert assays disclosed herein into an on-site detection system. In accordance with these embodiments, kits can contain one or more composition, agent or component needed to adapt assays disclosed herein to a hand-held device. In certain embodiments, a hand-held device can be included in a kit, capable of illuminating reaction tubes to detect a measurable fluorescent signal to assess assay outcomes. In some embodiments, fluorescent probes can be visualized through; for example, a handheld device, that excites the fluorophore with a specific wavelength light and fluorescence can be visualized through a film or window that allows certain wavelengths to pass through. In certain embodiments, concentrations of labeled RNA can be increased, as necessary, to provide fluorescence signals easily visible to the human eye. In accordance with these embodiments, kits can include one or more fluoride riboswitches disclosed herein where varied or changing fluoride concentrations can be differentiated by visual detection by an observer over a predetermined period of reaction time. In accordance with these embodiments, kits can include one or more zinc-response transcription factors where zinc concentrations in a sample can be differentiated by visual detection by an observer over a predetermined period of reaction time. In some embodiments, portable devices for detecting signals disclosed herein can be used by trained personnel to test samples from a subject for the presence and/or concentration of a target agent or analyte using compositions and methods disclosed herein.

In other embodiments, an agent-responsive component (e.g., zinc responsive factor) can be included in constructs disclosed herein to detect presence or concentration of an agent in a sample (e.g., from a subject or in water or soil or associated with vegetation such as an environmental sample) and presence and/or concentration can be detected using an illuminator device. In accordance with these embodiments, concentration of an agent-responsive component in a sample can be approximated by comparing fluorescence of one or more control samples to a calibration curve of the agent-responsive component as measured by visual analysis, by machine, or any combination thereof in order to assess concentration in the sample.

BRIEF DESCRIPTION OF THE DRAWINGS

The following drawings form part of the present specification and are included to further demonstrate certain embodiments of the present disclosure. Certain embodiments can be better understood by reference to one or more of these drawings in combination with the detailed description of specific embodiments presented herein.

DEFINITIONS

Figures 1A, 1B, 1C, 1D:
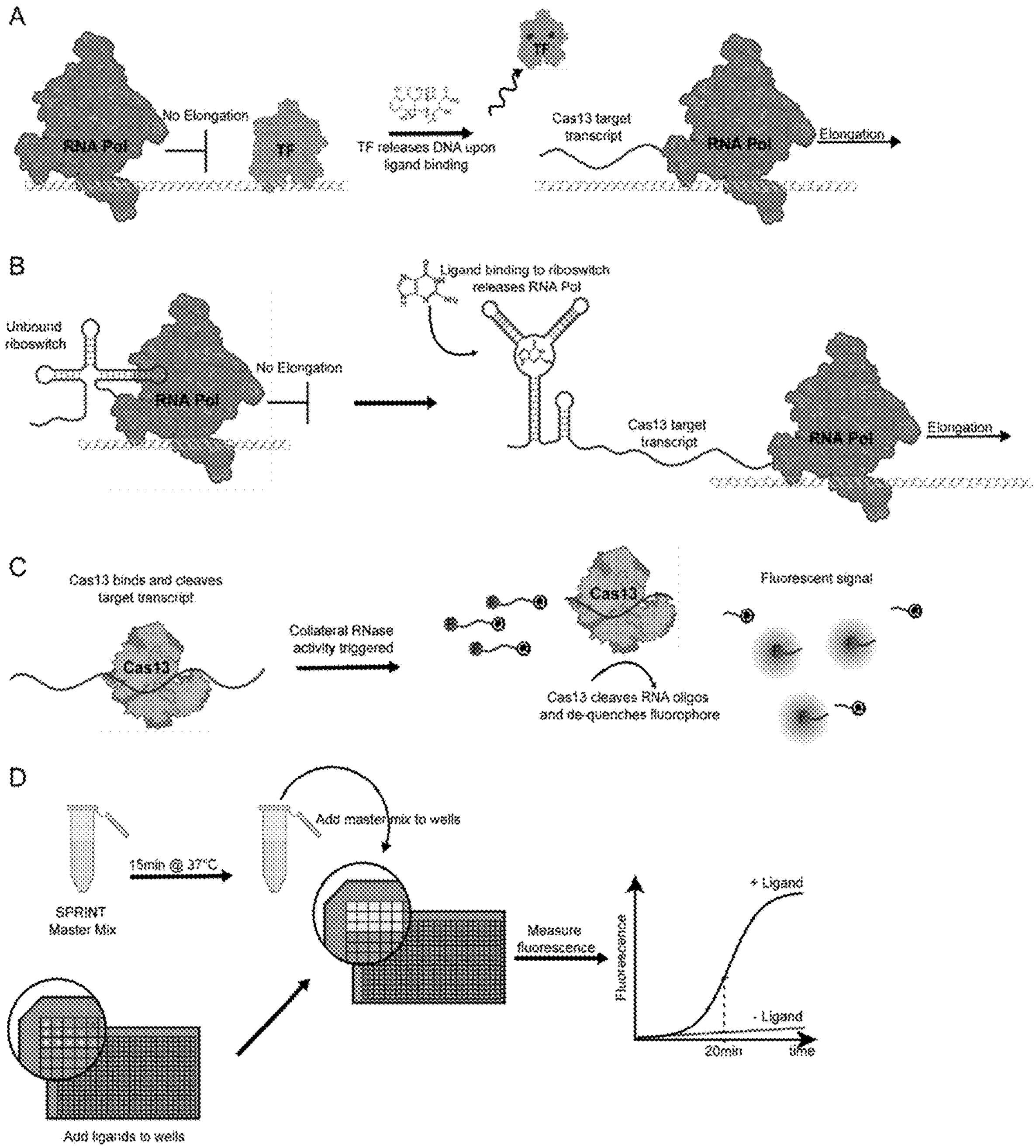
FIG. 1A illustrates a schematic of allosteric transcription factors that releases DNA from the DNA binding site when bound by ligand, therefore enabling transcript elongation in accordance with certain embodiments of the present disclosure.
FIG. 1B illustrates a schematic diagram of an exemplary assay including an ON-riboswitch allowing transcript elongation by RNA polymerase when the riboswitch is bound to its cognate ligand in accordance with certain embodiments of the present disclosure.
FIG. 1C illustrates an exemplary assay including a Cas13a that detects RNA transcripts containing a target sequence by collaterally cleaving RNA oligos and de-quenching fluorophores, and providing a fluorescent signal in accordance with certain embodiments of the present disclosure.
FIG. 1D illustrates workflow of an exemplary assay described herein where a composition containing components of RNA polymerase, Cas13a and a DNA template is incubated and provided to wells that contain compounds/reagents that regulate transcription before transcriptional output is measured by a fluorescence signal in accordance with certain embodiments of the present disclosure.

Terms, unless specifically defined herein, have meanings as commonly understood by a person of ordinary skill in the art relevant to certain embodiments disclosed herein or as applicable.

Unless otherwise indicated, all numbers expressing quantities of agents and/or compounds, properties such as molecular weights, reaction conditions, and as disclosed herein are contemplated as being modified in all instances by the term "about." Accordingly, unless indicated to the contrary, the numerical parameters in the specification and claims are approximations that may vary by about 10 to about 15% plus and/or minus depending upon the desired properties sought as disclosed herein. Numerical values as represented herein inherently contain standard deviations that necessarily result from the errors found in the numerical value's testing measurements.

As used herein, "individual," "subject," "host" and "patient" can be used interchangeably herein and refer to any mammalian subject for whom diagnosis, treatment, or therapy is desired, particularly humans.

As used herein, the term "analyte" can be construed broadly and can also include, but is not limited to, any compound, molecule (e.g. small molecule), agent, contemplated ion or other substance of interest to be detected, quantitated, identified, or characterized.

As used herein, the term "novel double-stranded DNA sequence" can refer to a double-stranded polynucleotide sequence that includes, but is not limited to, at least a transcriptional promoter, at least one regulatory element, and at least one target sequence.

As used herein, CRISPR RNA, or "crRNA" is understood to be synonymous with guide RNA or "gRNA" and the two terms are used interchangeably throughout the disclosure.

As used herein, the "CRISPR-associated bacterial enzyme C2c2" is understood to be synonymous with "Cas13" and the two terms are used interchangeably throughout the disclosure.

As used herein, a novel double-stranded DNA sequence can be referred to as a "SPRINT template" and assays disclosed herein including these constructs can be referred to as "SPRINT assays."

DETAILED DESCRIPTION OF THE INVENTION

In the following sections, various exemplary compositions and methods are described in order to detail various embodiments of the invention. It will be obvious to one skilled in the relevant art that practicing the various embodiments does not require the employment of all or even some of the details outlined herein, but rather that concentrations, times and other specific details can be modified through routine experimentation. In some cases, well known methods, or components have not been included in the description.

Embodiments of the instant disclosure relate to compositions, methods and systems for identifying a target molecule present in a sample (or concentrations of the target molecule) using quantification of transcription of RNA in a CRISPR-based assay approach. In certain embodiments, compositions disclosed herein can include a system for quantifying transcriptional output in a sample using rapid, reproducible and reliable assay methods. In certain embodiments, compositions disclosed herein can include compositions and systems for quantifying transcriptional output for detection or quantification of a target analyte in a sample using rapid, reproducible and reliable assay methods. In some embodiments, compositions and methods disclosed herein are comparable or an improvement to detection and quantification by state-of-the-art radiolabeling assays. In other embodiments, compositions and methods disclosed herein can provide an improvement over radiolabeling RNA quantification-based methods due to increased speed, increased efficiency, ease of use, high throughput of transcription assays, or any combination thereof. In other embodiments, compositions, methods and systems disclosed herein can provide an efficient combination of small-molecule dependent transcriptional regulation and a CRISPR-mediated RNA cleavage assay in a single efficient reaction.

In some embodiments, compositions and methods for improved quantification of transcriptional output can include a CRISPR-Cas or CRISPR system. As disclosed herein, a CRISPR-Cas system, can generally refer collectively to transcripts and other elements involved in expression of or directing the activity of CRISPR-associated ("Cas") genes which can include, but are not limited to, sequences encoding a Cas gene, a tracr (trans-activating CRISPR) sequence (e.g., tracrRNA or an active partial tracrRNA), a tracr-mate sequence (e.g., encompassing a "direct repeat" and a tracrRNA-processed partial direct repeat in the context of an endogenous CRISPR system), a guide sequence (also referred to as a "spacer" in the context of an endogenous CRISPR system), or "RNA(s)" as used herein (e.g., RNA(s) to guide Cas, e.g. CRISPR RNA and transactivating (tracr) RNA or a single guide RNA ((sgRNA) (chimeric RNA)) or other sequences and transcripts from a CRISPR locus. In certain embodiments, a CRISPR system contemplated herein can be characterized by elements that promote formation of a CRISPR complex at the site of a target sequence. As used herein, "target sequence" or "target analyte" can refer to a desired sequence (polynucleotide) or analyte to which a guide sequence can be designed to have complementarity, where hybridization or binding between a target sequence or target analyte and a guide sequence promotes the formation of a CRISPR complex. In some embodiments, a target sequence or target analyte herein can include RNA polynucleotides, DNA polynucleotides (single or double-stranded) or other agents or small molecules such as contaminants or other agents; for example, that can be detected or traced using compositions, systems and methods disclosed herein. The term “target RNA sequence” or “target polynucleotide sequence” can refer to a RNA polynucleotide being and/or including the target sequence. In accordance with these embodiments, a target RNA disclosed herein can be an RNA polynucleotide or a part of an RNA polynucleotide to which at least part of the crRNA is designed to have complementarity and where effector function mediated by the complex including a CRISPR effector protein and a crRNA is to be directed. A target sequence can be any sequence of interest to which a complementary sequence can be generated and used in compositions and methods disclosed herein.

In certain embodiments, a crRNA herein can target a site having about 70%, about 75%, about 80%, about 85% (e.g., about 85%, 90%, 95%, 99%, 100%) sequence similarity to SEQ ID NO: 18. In other embodiments, a crRNA herein can target a site having the sequence of SEQ ID NO: 18.

In some embodiments, a CRISPR system can include DNA targeting enzymes, including, but not limited to, Cas9 and Cas12a. In other embodiments, a CRISPR system can include RNA targeting enzymes, including but not limited to, Cas13. In accordance with these embodiments, where a CRISPR system includes the RNA targeting enzyme Cas13, the Cas13 protein can complex with crRNA by recognition of and association with, for example, a short hairpin in the crRNA, and target specificity can be encoded by a spacer that is complementary to the target region. As used herein, a targeting enzyme is also understood to be an effector protein.

In some embodiments, a Cas13 protein herein can target a site having about 70%, about 75%, about 80%, about 85% (e.g., about 85%, 90%, 95%, 99%, 100%) sequence homology to a polynucleotide represented by SEQ ID NO: 17. In some embodiments, a Cas13 protein herein can target a site having about 85, 90, 95, 99, or 100% homology to the polynucleotide sequence represented by SEQ ID NO: 17.

In addition to programmable RNase activity, Cas13s exhibit “collateral activity” after recognition and cleavage of a target transcript, leading to non-specific degradation of nearby transcripts (e.g. non-specific RNA sequences as disclosed herein and non-target RNA sequences for example) regardless of complementarity to the spacer. In accordance with these embodiments, a CRISPR system herein can have programmable RNase activity. In further accordance with these embodiments, a CRISPR system disclosed herein can have collateral RNase activity for degrading nearby transcripts contemplated herein (e.g. non-target RNA sequences).

In certain embodiments, an effector protein (e.g., a targeting enzyme) of a CRISPR RNA-targeting system disclosed herein can include at least one HEPN domain, including but not limited to, HEPN domains described herein, HEPN domains known in the art, and domains recognized to be HEPN domains by comparison to consensus sequence motifs. As used herein, a HEPN domain (higher eukaryotes and prokaryotes nucleotide-binding domain) refers to a region of approximately 110 amino acids found in the C terminus of sacsin, a chaperonin implicated in an early-onset neurodegenerative disease in human, and in many bacterial and archaea proteins. In some embodiments, a consensus sequence can be derived from the sequences of Cas13 orthologs provided herein. In other embodiments, an effector protein herein can include a single HEPN domain. In certain embodiments, an effector protein can include two HEPN domains or more HEPN domains. The terms “orthologue” (also referred to as “ortholog” herein) and “homologue” (also referred to as “homolog” herein) are well known in the art. By means of further guidance, a “homologue” of a protein as used herein can be a protein of the same species which performs the same or a similar function as the protein it is a homologue of. Homologous proteins can be, but are not required to be structurally related, or can be only partially structurally related. An “orthologue” of a protein as used herein can be a protein of a different species which performs the same or a similar function as the protein it is an orthologue of. Orthologous proteins can be, but are not required to be structurally related, or can be only partially structurally related.

In certain embodiments, an effector protein contemplated herein can be a type VI CRISPR-Cas effector protein. In some embodiments, a type VI CRISPR-Cas effector can be Cas13. In other embodiments, a type VI CRISPR-Cas effector can be Cas13a, Cas13b, Cas13c, Cas13d, or a combination thereof or the like. In some other embodiments, the homologue or orthologue of a Type VI effector protein such as referred to herein can have a sequence homology or identity of at least about 70%, about 75%, about 80%, about 85% (e.g., about 85%, 90%, 95%, 99%, 100%) with a Type VI protein such as Cas13a (e.g., based on the wild-type sequence of any of genus or species of bacteria).

As disclosed herein, regarding formation of a CRISPR complex, a “target RNA sequence” can refer to an RNA sequence where a guide sequence is designed to have complementarity, where hybridization between a target RNA sequence and a guide sequence promotes the formation of a CRISPR complex. In some embodiments, a target RNA sequence herein can include one or more RNA polynucleotides. The term “target RNA” herein can refer to a RNA polynucleotide being or including the target sequence of interest. In accordance with embodiments herein, a target RNA can be an RNA polynucleotide or a part of an RNA polynucleotide to which a part of the gRNA, e.g. the guide sequence, can be designed to have complementarity and to which the effector function mediated by the complex including CRISPR effector protein and a gRNA is to be directed. As disclosed herein, a “target sequence” can refer to a DNA sequence or DNA polynucleotide which encodes a target RNA sequence and optionally, other polynucleotides linked to the target RNA sequence.

In certain embodiments, a target sequence can be an RNA or DNA polynucleotide of about 10 to about 500 nucleotides (nts) or more in length, or about 10 to about 400 nts, or about 10 to about 300 nts, or about 10 to about 200 nts, or about 10 to about 150 nts, or about 10 to about 100 nts, or about 20 to about 80 nts, or about 20 to about 60 nts or about 30 nts in length or other suitable link to which a complementary or partially complementary sequence can be generated and found in a CRISPR RNA bound to the Cas protein disclosed herein. In accordance with these embodiments, a target sequence can be any polynucleotide of a target agent or molecule of interest to be detected and/or concentrations measured by compositions, systems and methods disclosed herein. In accordance with these embodiments, a target polynucleotide can be embedded within the transcribed RNA. In other embodiments, the target sequence is complementary to CRISPR RNA bound to the Cas protein.

In some embodiments, a novel double-stranded DNA sequence as disclosed herein can include a transcriptional promoter. In some embodiments, a transcriptional promoter can be constitutively active. Examples of transcriptional promoters suitable for use herein can include, but are not limited to, tac, T7A1, pol I, pol II, pol III, T7, U6, H1, retroviral Rous sarcoma virus (RSV) LTR promoter, cytomegalovirus (CMV) promoter, SV40 promoter, dihydrofolate reductase promoter, β-actin promoter, phosphoglycerol kinase (PGK) promoter, EF 1α promoter, U6 promoter, and the like. In some embodiments, a transcriptional promoter can be a RNA polymerase promoter. In some embodiments, a RNA polymerase promoter can be a tac promoter for *E. coli* RNAP. In accordance with these embodiments, an RNA polymerase promoter can be a tac promoter for *E. coli* RNAP having about 70%, about 75%, about 80%, about 85% (e.g., about 85%, 90%, 95%, 99%, 100%) sequence homology with the polynucleotide represented by SEQ ID NO: 15. In accordance with these embodiments, a RNA polymerase promoter can be a tac promoter for *E. coli* RNAP represented by SEQ ID NO: 15. In some embodiments, a RNA polymerase promoter can be a T7 promoter for T7 RNA polymerase. In accordance with these embodiments, a RNA polymerase promoter can be a T7 promoter having about 70%, about 75%, about 80%, about 85% (e.g., about 85%, 90%, 95%, 99%, 100%) sequence homology with the polynucleotide represented by SEQ ID NO: 16. In accordance with these embodiments, a RNA polymerase promoter can be a T7 promoter of SEQ ID NO: 16. In other embodiments, a transcriptional promoter can be operably linked to a functional domain. Functional domains suitable for use herein can include, but are not limited to, transcriptional initiators, transcriptional activators, transcriptional repressors, transcription factors (e.g., chemically regulated), transcriptional stabilizers, nucleases (e.g., ribonucleases), spliceosomes, beads, light inducible/controllable domains, chemically inducible/controllable domains, and the like.

In some embodiments, a novel double-stranded DNA sequence as disclosed herein can include a riboswitch. As used herein, a "riboswitch" can be a regulatory segment of a messenger RNA that is capable of binding metabolites, small molecules or monatomic ions as ligands and regulate mRNA expression by forming alternative structures in response to this binding. As used herein, a "monatomic ion" is understood to be an ion consisting of one atom. In some embodiments, a monatomic ion can be a type I binary ionic compound. In accordance with these embodiments, a type I binary ionic compound can be a metal (cation) that forms only one type of ion. Non-limiting examples of type I binary ionic compounds suitable for use in compositions and methods disclosed herein include lithium ($Li^+$), sodium ($Na^+$), potassium ($K^+$), rubidium ($Rb^+$), cesium ($Cs^+$), magnesium ($Mg^{2+}$), calcium ($Ca^{2+}$), strontium ($Sr^{2+}$), barium ($Ba^{2+}$), aluminium ($Al^{3+}$), silver ($Ag^+$), zinc ($Zn^{2+}$), and the like. In some embodiments, a monatomic ion can be an anion. Non-limiting examples of anions include hydride ($H^-$), fluoride ($F^-$), chloride ($Cl^-$), bromide ($Br^-$), iodide ($I^-$), oxide ($O^{2-}$), sulfide ($S^{2-}$), nitride ($N^{3-}$), phosphide ($P^{3-}$), and the like. In some embodiments, a monatomic ion can include a type II ionic compound. A type II ionic compound contains a metal that forms more than one type of ion, i.e., ions with different charges. Non-limiting examples of type II ionic compounds include iron(II) ($Fe^{2+}$) ferrous, iron(III) ($Fe^{3+}$) ferric, copper(II) ($Cu^{2+}$) cupric, copper(I) ($Cu^+$) cuprous, and the like. In some embodiments, gold and/or lead can be detected in a sample herein. In some embodiments, a monatomic ion can be an anion.

In some embodiments, a regulatory element can include a riboswitch. In accordance with these embodiments, riboswitches of use in compositions, methods and systems disclosed herein can be a lysine riboswitch, a glycine riboswitch, adenine riboswitch, TPP tandem riboswitch, and the like. In certain embodiments, a riboswitch herein can be a metabolite-dependent RNA switch. Non-limiting examples of metabolite-dependent riboswitches for use herein include A-box, B12 riboswitch, FMN-box, G-box, Gly-box, L-box, M-box, preQ1 riboswitch, ribozyme (e.g., glmS), S-box, Thi-box, YdaO riboswitch, YkkC riboswitch (e.g., ykkC-ykkD, yxkD), yybP-ykoY motif (e.g., yybP, ykoY), and the like.

In some embodiments, metabolites sensed by riboswitches can be, but are not limited to, amino acids, peptides, nucleic acids, acylcarnitines, monosaccharides, lipids and phospholipids, prostaglandins, hydroxyeicosatetraenoic acids, hydroxyoctadecadienoic acids, steroids, bile acids and glycolipids, phospholipids, and the like. In other embodiments, amino acids can be proteogenic, non-proteogenic amino acids, or a combination thereof. In some embodiments, lipids can be selected from at least one of the following lipid subtypes: glycerophospholipids, sphingolipids, and glycosphingolipids. Ligands sensed by riboswitches include, but are not limited to, magnesium, manganese, fluoride, nickel, or cobalt ions, nucleic acids such as guanine, adenine, prequeuosine-1, 2-deoxyguanosine, cyclic di-GMP, cyclic di-AMP, cyclic AMP-GMP, or ZTP, enzyme cofactors such as adenosylcobalamin, aquacobalamin, thiamin pyrophosphate, flavin mononucleotide, S-adenosylmethionine, molybdenum cofactor, tungsten cofactor, tetrahydrofolate, S-adenosylhomocysteine, amino acid residues and derivatives such as lysine, glycine, or glutamine, serotonin, or 5-hydroxytryptophan, and other metabolites such as glucosamine-6-phosphate, azaaromatics, or guanidine.

In other embodiments, a regulatory element of a novel double-stranded DNA sequence can be a riboswitch. In accordance with these embodiments, a riboswitch of use in novel double-stranded DNA sequences disclosed herein can be endogenous, naturally-occurring or synthetic. In some embodiments, a riboswitch herein can be exogenous to one or more organisms. In other embodiments, an endogenous riboswitch can be present in bacteria, archaea, plants, and/or fungi. In certain embodiments, a riboswitch herein can have about 70%, about 75%, about 80%, about 85% (e.g., about 85%, 90%, 95%, 99%, 100%) sequence homology with the polynucleotide represented by sequence similarity to one or more *Bacillus* spp. riboswitches. In some embodiments, a riboswitch encoded in novel double-stranded DNA sequences as disclosed herein can be a member of the SAM riboswitch family, the purine riboswitch family, the guanine riboswitch family, the fluoride riboswitch family, the adenine riboswitch family, the flavin mononucleotide (FMN) riboswitch family, the lysine riboswitch family, the $Mg^{2+}$/ykoK family or a combination thereof. Non-limiting examples of riboswitches can include cobalamin riboswitches, cyclic AMP-GMP riboswitches, cyclic di-AMP riboswitches, cyclic di-GMP riboswitches, fluoride riboswitches, flavin mononucleotide (FMN) riboswitches, glmS riboswitches, glutamine riboswitches, glycine riboswitches, lysine riboswitches, manganese riboswitches, NiCo (nickel-cobalt) riboswitches, pre-queuosine1 (PreQ1) riboswitches, purine riboswitches, S-adenosylhomocysteine (SAH) riboswitches, S-adenosyl methionine (SAM) riboswitches, SAM-SAH riboswitches, Tetrahydrofolate riboswitches, ZMP/ZTP riboswitches, and the like. In some embodiments, a riboswitch can be a riboswitch candidate with at least one of the preceding criteria: crcB RNA Motif, manA RNA motif, pfl RNA motif, ydaO/yuaA leader, yjdF RNA motif, ykkC-yxkD leader (and related ykkC-III RNA motif) and the yybP-ykoY leader. In certain embodiments, riboswitches disclosed herein can include xpt/pbuE*6U, ribD/pbuE* 7U, yitJ/pbuE* 6U, pbuE/pbuE‡, crcB, P1/ pbuE'7U and metE or similar.

In certain embodiments, a riboswitch can be a guanine riboswitch having an aptamer with about 70%, about 75%, about 80%, about 85% (e.g., about 85%, 90%, 95%, 99%, 100%) sequence homology with the polynucleotide represented by SEQ ID NO: 20. In some embodiments, a riboswitch herein can be a guanine riboswitch having an aptamer with SEQ ID NO: 20. In some embodiments, a riboswitch herein can be a guanine riboswitch having about 70%, about 75%, about 80%, about 85% (e.g., about 85%, 90%, 95%, 99%, 100%) sequence homology with the polynucleotide represented by SEQ ID NO: 19. In some embodiments, a riboswitch herein can be a guanine riboswitch having about 85%, 90%, 95%, 99%, 100% sequence homology to the polynucleotide represented by SEQ ID NO: 19.

In some embodiments, a riboswitch herein can be a FMN riboswitch having an aptamer having about 70%, about 75%, about 80%, about 85% (e.g., about 85%, 90%, 95%, 99%, 100%) sequence homology with the polynucleotide represented by SEQ ID NO: 22. In some embodiments, a riboswitch herein can be a FMN riboswitch having an aptamer having about 85%, 90%, 95%, 99%, 100% sequence homology to the polynucleotide represented by SEQ ID NO: 22. In some embodiments, a riboswitch herein can be a FMN riboswitch having about 70%, about 75%, about 80%, about 85% (e.g., about 85%, 90%, 95%, 99%, 100%) sequence homology with the polynucleotide represented by SEQ ID NO: 21. In some embodiments, a riboswitch herein can be a FMN riboswitch having an aptamer having about 85%, 90%, 95%, 99%, 100% sequence homology to the polynucleotide represented by SEQ ID NO: 21.

In some embodiments, a riboswitch herein can be a SAM riboswitch having an aptamer riboswitch having about 70%, about 75%, about 80%, about 85% (e.g., about 85%, 90%, 95%, 99%, 100%) sequence homology with the polynucleotide represented by SEQ ID NO: 24. In some embodiments, a riboswitch herein can be a SAM having about 85%, 90%, 95%, 99%, 100% sequence homology to the polynucleotide represented by SEQ ID NO: 24. In some embodiments, a riboswitch herein can be a SAM riboswitch having about 70%, about 75%, about 80%, about 85% (e.g., about 85%, 90%, 95%, 99%, 100%) sequence homology with the polynucleotide represented by SEQ ID NO: 23. In some embodiments, a riboswitch herein can be a SAM riboswitch having about 85%, 90%, 95%, 99%, 100% sequence homology to the polynucleotide represented by SEQ ID NO: 23. In some embodiments, a riboswitch herein can be a SAM riboswitch having an aptamer riboswitch having about 70%, about 75%, about 80%, about 85% (e.g., about 85%, 90%, 95%, 99%, 100%) sequence homology with the polynucleotide represented by SEQ ID NO: 28. In some embodiments, a riboswitch herein can be a SAM riboswitch having about 85%, 90%, 95%, 99%, 100% sequence homology to the polynucleotide represented by SEQ ID NO: 28.

In some embodiments, a riboswitch herein can be an adenine riboswitch having about 70%, about 75%, about 80%, about 85% (e.g., about 85%, 90%, 95%, 99%, 100%) sequence homology with the polynucleotide represented by SEQ ID NO: 26. In some embodiments, a riboswitch herein can be an adenine riboswitch having an aptamer having about 85%, 90%, 95%, 99%, 100% sequence homology to the polynucleotide represented by SEQ ID NO: 26. In some embodiments, a riboswitch herein can be an adenine riboswitch having about 70%, about 75%, about 80%, about 85% (e.g., about 85%, 90%, 95%, 99%, 100%) sequence homology with the polynucleotide represented by SEQ ID NO: 25. In some embodiments, a riboswitch herein can be an adenine riboswitch having about 85%, 90%, 95%, 99%, 100% sequence homology to the polynucleotide represented by SEQ ID NO: 25.

In some embodiments, a riboswitch can be a synthetic riboswitch. The term "synthetic" indicates that the riboswitch has been prepared in whole or in part by human intervention, and is not a compound naturally produced by a naturally occurring organism or endogenous to a species. In accordance with these embodiments, a segment to the complete riboswitch can be a synthetic riboswitch produced by an organism, and then subsequently modified by synthetic methods to produce a non-naturally occurring riboswitch. In accordance with these embodiments, a riboswitch can be prepared by synthetic methods, and the resulting molecule can be fully synthetic. Non-limiting examples of synthetic riboswitches for use herein include synthetic theophylline riboswitches, synthetic neomycin riboswitches, synthetic ciprofloxacin riboswitches, synthetic paromomycin riboswitches, synthetic tetracycline riboswitches, and the like. Other synthetic riboswitches are contemplated of use in constructs and systems disclosed herein.

In some embodiments, a novel double-stranded DNA sequence as disclosed herein can include an allosteric transcription factor (aTF) operator sequence. In accordance with these embodiments, allosteric transcription factors (aTFs) can encompass several large families of proteins that provide environmental response in bacteria. In accordance with embodiments herein, aTFs can undergo a conformational change upon binding a small molecule that alters their affinity for an operator DNA sequence that can often be found upstream of regulated metabolic operons or transporter genes. In some embodiments, an aTF operator sequence herein can target a repressor aTF. In certain embodiments, an aTF operator sequence herein can target a de-repressor aTF, wherein de-repressors can release their DNA binding site when they are bound by ligand, therefore enabling transcript elongation. In some embodiments, a de-repressor aTF can be tetR or smtB.

In some embodiments, an aTF operator sequence herein can be a zinc aTF operator sequence. In some embodiments, an aTF operator sequence herein can be a zinc aTF operator sequence w having about 70%, about 75%, about 80%, about 85% (e.g., about 85%, 90%, 95%, 99%, 100%) sequence homology with the polynucleotide represented by SEQ ID NO: 29. In some embodiments, an aTF operator sequence herein can be a zinc aTF operator sequence having about 85%, 90%, 95%, 99%, 100% sequence homology to the polynucleotide represented by SEQ ID NO: 29.

In some embodiments, an aTF operator sequence herein can be a tetracycline aTF operator sequence. In some embodiments, an aTF operator sequence herein can be a tetracycline aTF operator sequence having about 70%, about 75%, about 80%, about 85% (e.g., about 85%, 90%, 95%, 99%, 100%) sequence homology with the polynucleotide represented by SEQ ID NO: 30. In some embodiments, an aTF operator sequence herein can be a tetracycline aTF operator sequence having about 85%, 90%, 95%, 99%, 100% sequence homology to the polynucleotide represented by SEQ ID NO: 30.

In some embodiments, novel double-stranded DNA sequences (e.g., SPRINT templates) disclosed herein can have a constant 5' region with tac promoter for *E. coli* RNAP. In some embodiments, novel double-stranded DNA sequences disclosed herein can have a constant 5' region with tac promoter for *E. coli* RNAP having about 70%, about 75%, about 80%, about 85% (e.g., about 85%, 90%, 95%, 99%, 100%) sequence homology with the polynucleotide represented by SEQ ID NO: 31. In some embodiments, novel double-stranded DNA sequences disclosed herein can have a constant 5' region with tac promoter for *E. coli* RNAP having about 85%, 90%, 95%, 99%, 100% sequence homology to the polynucleotide represented by SEQ ID NO: 31.

In some embodiments, novel double-stranded DNA sequences (e.g., SPRINT templates) disclosed herein can have a constant 3' region with a sequence for target RNA (ssRNA1). In some embodiments, novel double-stranded DNA disclosed herein can have a constant 3' region with a sequence for target RNA (ssRNA1) having about 70%, about 75%, about 80%, about 85% (e.g., about 85%, 90%, 95%, 99%, 100%) sequence homology with the polynucleotide represented by SEQ ID NO: 33. In some embodiments, novel double-stranded DNA disclosed herein can have a constant 3' region with a sequence for target RNA (ssRNA1) having about 85%, 90%, 95%, 99%, 100% sequence homology to the polynucleotide represented by SEQ ID NO: 33.

In some embodiments, novel double-stranded DNA sequences (e.g., SPRINT templates) disclosed herein having about 70%, about 75%, about 80%, about 85% (e.g., about 85%, 90%, 95%, 99%, 100%) sequence homology with the polynucleotide represented by any one of SEQ ID NOs: 36-45. In some embodiments, novel double-stranded DNA sequences (e.g., SPRINT templates) disclosed herein have about 85%, 90%, 95%, 99%, 100% sequence homology to the polynucleotide represented by any one of SEQ ID NOs: 36-45.

In some embodiments, a novel double-stranded DNA sequence disclosed herein can encode any RNA structure as part of the regulatory element in place of an aptamer. In certain embodiments, structural elements in RNA can include secondary structural motifs, tertiary structural motifs, or a combination thereof. Non-limiting examples of structural elements in RNA include stem-loops (hairpins), internal loops, bulges, pseudoknots, kink-turns, g-quadruplexes, and the like. In accordance with embodiments herein, binding of a drug-like compound to a tertiary structure of an RNA herein can regulate transcriptional output and, in turn, fluorescent signal for determination of drug effects and screening purposed. In some embodiments, binding of a drug-like compound to an RNA structure herein can be observed through one or more fluorescent signals. In accordance with these embodiments, observing binding of a drug-like compound to an RNA structure herein by detection of one or more fluorescent signals can aid in screening drug and drug-like compounds as single agents, multiple agents or part of a drug library to identify which of agents can bind selected RNA structures.

In some embodiments, RNA structures that can be part of a regulatory element contemplated herein herein can be derived from an RNA structure of clinical interest. In other embodiments, RNA structures of clinical interest herein can be a human RNA structure of clinical interest. In some embodiments, human RNA structures of clinical interest herein can be an expansion repeat such as the CUG or CAG repeat expansions which are causative of certain health conditions, including, but not limited to, myotonic dystrophy and Huntington disease, respectively (e.g. small-molecule drugs against CUG repeats).

In certain embodiments, RNA structures that can form part of a regulatory element contemplated herein and of clinical interest herein can be a viral RNA structure. In accordance with these embodiments, RNA structures of interest herein can be a viral RNA structure such as an HIV TAR structure which can be targeted with a small-molecule inhibitor to alleviate symptoms of AIDS. In accordance with these embodiments, RNA structures of interest herein can be a viral RNA structure such as an SARS-CoV pseudoknot which can be targeted with a small-molecule inhibitor to fight viral infections (e.g., COVID-19). It is contemplated that any novel RNA structure associated with a pathogenic virus can be used in composition, methods and systems disclosed herein to detect presence, absence and/or level of the associating virus such as a pathogenic RNA virus.

In certain embodiments, RNA structures that can form part of a regulatory element contemplated herein and of clinical interest herein can be a bacterial RNA structure. In accordance with these embodiments, RNA structures of clinical interest herein can be a bacterial RNA structure such as a 23S rRNA which can be targeted with a small-molecule inhibitor (e.g., linezolid) to fight bacterial infections. In accordance with these embodiments, RNA structures of clinical interest herein can be a bacterial RNA structure such as a FMN (flavin mononucleotide) riboswitch which can be targeted with a small-molecule (e.g., ribocil) to fight bacterial infections.

In some embodiments, synthetic RNA structures herein can be a variant of a human RNA structure where the difference in RNA structure is related to at least one sequence variance. In some embodiments, DNA transcription templates as disclosed herein can include a human RNA sequence in which at least one sequence variance provides a difference in secondary structure and wherein allele specificity can involve that difference in secondary structure. In other embodiments, at least one sequence variance providing a difference in secondary structure can be associated with at least one human disease.

Embodiments of the instant disclosure relate methods for generating the novel double-stranded DNA sequences (e.g., SPRINT templates) disclosed herein. In certain embodiments, any of the novel double-stranded DNA sequences disclosed herein can be produced via, e.g., conventional recombinant technology or technology for creating a double-stranded DNA sequence. In some examples, double-stranded DNA sequences disclosed herein can be readily isolated and sequenced using conventional procedures (e.g., by using oligonucleotide probes that are capable of binding specifically to genes encoding a polypeptide sequence). Once isolated, the nucleic acid sequences herein can be placed into one or more expression vectors, which can then be transfected into host cells for example, prokaryote or eukaryote or other host cell systems. In accordance with these embodiments, a host cell can include, but is not limited to, *E. coli* cells, simian COS cells, Chinese hamster ovary (CHO) cells, Human Embryotic Kidney (HEK) 293 cells or myeloma cells that do not otherwise produce the proteins, protein domains, peptides, peptide fragments, and/or polypeptides encoded by the nucleic acid sequences disclosed herein. In some embodiments, an expression vector for use herein can be a pUC or pBR plasmid. In some embodiments, nucleic acid sequences can then be modified accordingly for generating any of the compositions disclosed herein.

In some embodiments, a system for quantifying transcriptional output in a sample as disclosed herein can include a fluorescently labeled RNA oligonucleotide having a non-target sequence. In other embodiments, a fluorescently labeled RNA oligonucleotide having a non-target sequence can be subjected to "collateral activity" after an effector protein as disclosed herein is activated where the non-target sequence can be degraded. In certain embodiments, a fluorescently labeled RNA oligonucleotide as disclosed herein can include a fluorophore attached to one end of the oligonucleotide. In some embodiments, the fluorophore can be, but is not limited to, fluorescein, fluorescein isothiocyanate (FITC), carboxyfluorescein (FAM), 6-carboxyfluorescein (6-FAM), rhodamine dye, TEX 615, Texas red, CAL Fluor 610, or other suitable fluorophore detectable by a machine or human eye of use in the disclosed constructs, methods and systems. In other embodiments, a fluorescently labeled RNA oligonucleotide as disclosed herein can include a quencher attached to at least one end of the oligonucleotide. In some embodiments, the quencher can be, but is not limited to, Iowa Black, Black Hole Quencher 1, Black Hole Quencher 2, Dabcyl or any other suitable quenching agent capable of pairing with a fluorophore contemplated herein and quenching a signal output. In some embodiments, a fluorescently labeled RNA oligonucleotide as disclosed herein can have a fluorophore attached to the 5' end of the oligonucleotide and a quencher attached to the 3' end of the oligonucleotide. In some embodiments, a fluorescently labeled RNA oligonucleotide as disclosed herein can have a fluorophore attached to the 3' end of the oligonucleotide and a quencher attached to the 5' end of the oligonucleotide. In accordance with these embodiments, upon activation of any effector proteins disclosed herein, an RNA oligonucleotide can be cleaved, severing the proximity between the fluorophore and quencher needed to maintain a contact quenching effect. In accordance with these embodiments, detection of a fluorophore can be used to determine the presence and/or quantity of a target molecule in a sample. In accordance with these embodiments, depending on the presence and/or level of the detected target molecule, a subject may undergo treatment and further analysis by these methods or a measure can be taken to reduce the presence of a target molecule or enhance the presence of a target molecule, depending on the circumstances.

In certain embodiments, a target molecule contemplated to be assessed in a sample herein can be a bacterium, derived from a bacterium or a toxin of a bacterium affecting a human, mammal, bird or in the environment, including but not limited to, a toxin derived from, *Pasteurella haemolytica, Clostridium difficile, Clostridium haemolyticum, Clostridium tetani, Corynebacterium diphtheria, Neorickettsia resticii, Streptococcus equi equi, Streptococcus pneumoniae, Salmonella* spp., *Chlamydia trachomatis, Bacillus anthracis, Yersinia* spp., and *Clostridium botulinum* or any combinations thereof. In yet other embodiments, a target molecule contemplated to be assessed in a sample disclosed herein can be a toxin, such as ricin toxin or botulinum toxin or anthrax toxin.

In some embodiments, a system for quantifying transcriptional output in a sample herein can be used to determine presence of at least one contaminant in an environmental sample. In other embodiments, an environmental sample disclosed herein can include, without limitation, samples obtained from the environment, including soil (e.g., rhizosphere), air, water (e.g., marine water, fresh water, rain water, wastewater sludge, runoff), sediment, oil, an extreme environmental sample (e.g., acid mine drainage, hydrothermal systems) and any combinations thereof. In accordance with these embodiments, marine or freshwater samples can be from the surface of the body of water, or any depth of the body of water, e.g., a deep sea sample. In accordance with these embodiments, a water sample can be an ocean, a sea, a river, a lake, or a sewage sample. In accordance with these embodiments, a water sample can be sourced from a water-treatment facility, a sewage facility, or any building in need thereof.

In some embodiments, a system for quantifying transcriptional output in a sample herein can be used to determine the presence of at least one contaminant in a soil sample, a water sample, an air sample, or a combination thereof. In some embodiments, a system for determining presence and/or quantifying transcriptional output in a sample herein can be used to identify and control waterborne disease and outbreak. In accordance with these embodiments, identification and control of waterborne disease and outbreak can provide information to be used to prevent contamination, illness, future disease outbreaks, and the like. In some embodiments, a system for quantifying transcriptional output in a sample herein can be used to determine presence of a water outbreak by monitoring the activity of *Giardia, Legionella, Shigella, Norovirus, Campylobacter, Cryptosporidium, Pseudomonas, E. coli*, or other water contaminant, or any combination thereof.

In some embodiments, a system for quantifying transcriptional output in a sample herein can be used to monitor microbiome communities in soil. In accordance with these embodiments, microbiomes, communities of bacteria, viruses, and other microbes, subjected to systems herein can found in and/or on all known multicellular organisms. In other embodiments, a system for quantifying transcriptional output in a sample herein can be used to monitor and/or manipulate ecosystem processes controlled by microbiome communities such as, but not limited to, nutrient cycling, organic matter turnover, and the development or inhibition of soil pathogens. As used herein, the term "microbiome" refers to either the collective genomes of prokaryotic organisms that reside in an environmental niche or the collective genomes microorganisms themselves for example, a mammalian stomach microbiome. In accordance with these embodiments, a microbiome subjected to systems herein can include collective genomes of one or more prokaryotic organisms selected from bacteria, archaea, protists, fungi, viruses, or any combination thereof. Any prokaryotic organisms known to those skilled in the art are within the scope of the present disclosure. In some non-limiting embodiments, prokaryotic organisms include bacterial organisms, archaeal organisms, and combinations thereof. In other non-limiting embodiments, prokaryotic organisms include bacterial organisms, bacterial species, or strains of bacterial species. In still other non-limiting embodiments, the prokaryotic organisms include archaeal organisms, archaeal species, or strains of archaeal species. In some embodiments, a system for quantifying transcriptional output in a sample herein can be used to measure the impact of soil microbes on the productivity of natural plant communities, agroecosystems, sanitation infrastructures, or a combination thereof.

In some embodiments, a system for quantifying transcriptional output in a sample herein can be used to monitor microbiome communities in the gut or gastrointestinal tract of a subject. In accordance with these embodiments, monitoring microbiome communities in the gut or gastrointestinal tract of a subject according to the methods herein can identify one or more disruptions of a natural microbiome that can result in serious health conditions including, but not limited to, infectious diseases, cancers, and complex disorders such as Crohn's disease, ulcerative colitis, and diabetes, and the like. In accordance with these embodiments, monitoring microbiome communities in the gut or gastrointestinal tract of a subject according to the methods herein can identify one or more disruptions of a natural microbiome requiring interventional manipulations of the microbiota, either by probiotics, prebiotics, fecal transplantation, or any combination thereof. In accordance with these embodiments, monitoring microbiome communities in the gut or gastrointestinal tract of a subject according to the methods herein can predict one or more abnormal health statuses of a subject (e.g. a human subject). In accordance with these embodiments, monitoring microbiome communities in the gut or gastrointestinal tract of a subject according to the methods herein can diagnose one or more diseases in a subject (e.g. a human subject). In some embodiments, monitoring microbiome communities in the gut or gastrointestinal tract of a subject according to the methods herein can diagnose one or more diseases in a subject (e.g. a human subject) sooner that clinical diagnosis methods standard in the art. In other embodiments, monitoring microbiome communities in the gut or gastrointestinal tract of a subject according to the methods herein can predict one or more diseases in a subject (e.g. a human subject). In some embodiments, a system for qualifying and/or quantifying transcriptional output in a sample herein can be used to identify interventional manipulations and/or educational assessment of the microbiota of a subject. In some embodiments, a system for quantifying transcriptional output in a sample herein can be used in early disease diagnosis and/or prevention to characterize and monitor a subject's microbiome.

In some embodiments, samples disclosed herein can be obtained from any source known to those skilled in the art. In some non-limiting embodiments, a sample can be obtained from soil, air, water (including, without limitation, marine water, fresh water, and rain water), sediment, oil, and combinations thereof. In other non-limiting embodiments, a microbiome sample can be obtained from a subject selected from a protozoan, an animal (e.g., a mammal, e.g., human), or a plant. In some embodiments, samples disclosed herein can biological samples. The term "biological sample" can include a sample obtained from subject (e.g., a bodily fluid, a tissue). Non-limiting biological samples obtained from subject suitable for use herein can include blood, sputum, plasma, serum, cell scrapings, tissues, biopsies, teeth, perspiration, fingernail, skin, hair, feces, urine, semen, mucus, saliva, gastrointestinal tract samples, and the like. In accordance with these embodiments, a biological sample can be obtained using any method known by one of skill in the art.

The term "subject" as used herein refers to an animal, including but not limited to a mammal including a human, a non-human primate (for example, a monkey or great ape), a cow, a pig, a cat, a dog, a rat, a mouse, a horse, a goat, a rabbit, a sheep, a hamster, a guinea pig, a rat, a mouse, a bird, a reptile, a worm, a fish, or any other subject. In some embodiments, a subject can be a human such as an adult, a young child, adolescent, toddler, infant or fetus. In some embodiments, a subject can be at a genetic risk for development a condition or disease or has a condition or disease assessed by analyzing the presence or absence of a biomarker using compositions and methods disclosed herein. Non-limiting examples of such diseases or conditions include digestive system diseases, cardiovascular diseases, neurological diseases, obesity, infectious diseases, diabetes, vitamin deficiencies, nutritional deficiencies, cofactor deficiencies or overproduction regarding the same and cancers. In other embodiments, a subject can be at a risk of developing an infection by assessment of a biomarker indicator diagnoses, e.g., coronavirus, dengue virus, MERS, HPV, HIV, or any other infection. As disclosed herein, a target sequence can be one of use to detect levels or presence of a biomarker (e.g. a hormone or other indicator, a viral related agent, a disease related agent) in order to assess risk or other indicators of a condition.

In some embodiments, a sample obtained from an animal subject can be a body fluid such as urine, saliva, blood, gastrointestinal fluid, eye fluid or other body fluid obtained from a subject. In other embodiments, a sample obtained from an animal subject can be a tissue sample. Non-limiting samples obtained from an animal subject include tooth, perspiration, fingernail, skin, hair, feces, urine, semen, mucus, saliva, and gastrointestinal tract samples. In some embodiments, a sample can be a human microbiome sample that encompasses collection of microorganisms found on the surface and deep layers of skin, in mammary glands, saliva, oral mucosa, conjunctiva and gastrointestinal tract. In some aspects, microorganisms found in the microbiome can include bacteria, fungi, protozoa, viruses and/or archaea. In some embodiments, different parts of a subject's body can exhibit varying diversity of microorganisms. In some embodiments, quantity and/or type of microorganisms can signal a healthy state or a diseased state of a subject whose microbiome it was collected from. In some embodiments, a bacterial composition for a given site on a subject's body can vary from subject to subject, not only in type, but also in abundance or quantity.

In some embodiments, a system for quantifying transcriptional output in a sample as disclosed herein can include buffer reagents. Different components or reagents useful for amplification of nucleic acids are described herein and are known in the art. In accordance with these embodiments, any buffer capable of acting as reagents for compositions and methods disclosed herein can be contemplated. In some embodiments, an amplification reagent as described herein can include a buffer, such as a phosphate, or a Tris buffer. In accordance with these embodiments, a Tris buffer for use herein can be used at any applicable concentration, for example including, but not limited to, a concentration of less than about 1 mM, 1 mM, 2 mM, 3 mM, 4 mM, 5 mM, 6 mM, 7 mM, 8 mM, 9 mM, 10 mM, 11 mM, 12 mM, 13 mM, 14 mM, 15 mM, 25 mM, 50 mM, 75 mM, 1 M, or the like. One of skill in the art can determine an appropriate concentration of a buffer for use with the present invention.

In certain embodiments, buffer reagents disclosed herein can contain a salt, including, but not limited to, magnesium chloride ($MgCl_2$), potassium chloride (KCl), or sodium chloride (NaCl) or other suitable salt, can be part of an amplification reaction, such as PCR, in order to improve amplification of nucleic acid fragments. Although the salt concentration will depend on the particular reaction and application, in some embodiments, nucleic acid fragments of a particular size can produce optimum results at a salt concentration or a range of salt concentrations. In accordance with these embodiments, larger products herein can require altered salt concentrations, for example, a lower salt, in order to produce desired results, while amplification of smaller products here can produce better results at higher salt concentrations. One of skill in the art understands that the presence and/or concentration of a salt, along with alteration of salt concentrations, can alter stringency of a biological or chemical reaction, and therefore any salt can be used that provides the appropriate conditions for a reaction of the present invention and as described herein.

In certain embodiments, buffer reagents disclosed herein can contain at least one reducing agent. Non-limiting examples of reducing agents suitable for use herein include lithium aluminium hydride ($LiAlH_4$), nascent (atomic)

hydrogen, hydrogen without or with a suitable catalyst (e.g., a Lindlar catalyst), sodium amalgam (Na(Hg)), sodium-lead alloy (Na+Pb), zinc amalgam (Zn(Hg)), diborane, sodium borohydride ($NaBH_4$), sulfur dioxide, dithionates (e.g., $Na_2S_2O_6$), hydrogen peroxide ($H_2O_2$), diisobutylaluminium hydride (DIBAL-H), dithiothreitol (DTT), 2-Mercaptoethanol (β-mercaptoethanol), and the like.

In some embodiments, buffer reagents disclosed herein can contain at least one chelating agent. Non-limiting examples of chelating agents suitable for use herein include nitrilotriacetic acid (NTA), iminodisuccinic acid (IDS), polyaspartic acid, S,S-ethylenediamine-N,N'-disuccinic acid (EDDS), methylglycinediacetic acid (MGDA), and L-glutamic acid N,N-diacetic acid, tetrasodium salt (GLDA), ethylenediaminetetraacetic acid (EDTA), and the like.

In some other embodiments, compositions disclosed herein can be used in methods of detection using quantification of transcriptional output in a sample (e.g., from a subject and/or environmental sample). In some embodiments, compositions disclosed herein can be used in one or more in vitro transcription assays to assess ligand-dependent riboswitch function and/or regulation. In some embodiments, absence of ligand in a ligand-dependent riboswitch function assay can lead to repression of a fluorescent signal. In some other embodiments, presence of ligand in a ligand-dependent riboswitch function assay can lead to presence of a fluorescent signal. In some embodiments, strength of a fluorescent signal in a ligand-dependent riboswitch function or regulation assay can be indicative of multiple turnover transcriptions.

In some embodiments, an aptamer can be incorporated into the expression platform to generate a riboswitch for the specific aptamer. In accordance with these embodiments, an aptamer herein can be designed to target any analyte of interest and used in constructs, compositions, systems and/or methods disclosed herein. As used herein, an "aptamer" can be an oligonucleotide that is capable of binding to a specific target molecule. In some embodiments, aptamers for use in the present disclosure can be endogenous. In some other embodiments, aptamers for use in the present disclosure can be synthetic. In some embodiments, an aptamer with an affinity for at least one ligand can be incorporated into the expression platform to generate a riboswitch for the specific aptamer. In some certain embodiments, an aptamer that binds to the neurotransmitter serotonin (e.g. 5-hydroxytryptamine) can be incorporated into the expression platform to generate a riboswitch a riboswitch for serotonin. In some embodiments, riboswitch libraries can be selected or screened with the constructs, compositions, systems and/or methods disclosed herein to identify riboswitches, aptamers, and/or RNA structures responsive to a ligand of interest.

In some embodiments, compositions disclosed herein can be used to screen small compounds. In some embodiments, compositions disclosed herein can be used to measure whether a drug-like compound affects components of the transcriptional machinery. In accordance with these embodiments, components of the transcriptional machinery could include, but are not limited to transcriptional regulators such as riboswitches or transcription factors, and RNA polymerases. In accordance with these embodiments, measurements of such interactions could be used to screen compound libraries in order to identify compounds that interact with RNA structures or proteins present in viruses, bacteria or human cells that are of clinical interest. In some embodiments, compositions disclosed herein can be used to screen for drug-like compounds to achieve bactericidal effects. In some embodiments, compositions disclosed herein can be used as phenotypic screens to assess the efficacy of antibiotics.

In some embodiments, compositions disclosed herein can be used in the detection and quantification of biomarkers, e.g., metabolites, in biological samples, e.g., blood, serum, or plasma, in a clinical setting. As used herein, the term "biomarker" can refer to an agent whose presence, level, or form, correlates with a particular biological event or state of interest, so that it is considered to be a "marker" of that event or state. In certain embodiments, a biomarker can include a marker for a particular disease state, or for likelihood that a particular disease, disorder or condition may develop. In some embodiments, a biomarker may be or comprise a marker for a particular disease or therapeutic outcome, or likelihood thereof. In some embodiments, a biomarker can be predictive. In some embodiments, a biomarker can be prognostic. In some embodiments, a biomarker can be diagnostic of one or more relevant biological events, one or more health conditions, and/or one or more states of a subject's health. In accordance with these embodiments, a biomarker herein can be an agent of any chemical class. For example, in some embodiments, a biomarker can be a vitamin, a hormone, a neurotransmitter, a receptor, a nucleic acid, a polypeptide (e.g. an enzyme), a lipid, a carbohydrate, a small molecule, an inorganic agent (e.g., a metal or ion), or a combination thereof. In some embodiments, a biomarker herein can be a cell surface marker. In some embodiments, a biomarker herein can be intracellular. In some embodiments, a biomarker herein can be found outside of cells (e.g., is secreted or is otherwise generated or present outside of cells, e.g., in a body fluid such as blood, urine, tears, saliva, cerebrospinal fluid, etc.)

In certain embodiments, compositions disclosed herein can be used to monitor the activity of at least one enzyme. In some embodiments, enzymatic activity can cause conversion of substrate to product. In other embodiments, concentration of substrate or product can regulate transcriptional output. In accordance with these embodiments, differential transcriptional output can be quantified as fluorescent signal by the compositions disclosed herein. In some embodiments, enzymatic activity can be measured as transcriptional regulation by an enzymatically produced metabolite.

In some embodiments, compositions and methods disclosed herein can be used to monitor elements in environmental samples. In accordance with these embodiments, portable kits and/or devices can be used to test environmental samples according to methods disclosed herein. In other embodiments, compositions disclosed herein can be used to monitor fluoride and/or zinc in environmental water samples.

In certain embodiments, compositions disclosed herein can encompass kits used for transcriptional fluorescent output in in vitro samples. In some embodiments, compositions disclosed herein, in addition to kits encompassing disclosed compositions, can be used in conjunction with a diagnostic device. Non-limiting examples of diagnostic devices suitable for use herein include point-of-care diagnostic devices, portable systems (e.g., lateral flow assays (LFA)), and/or portable fluorescent detection devices.

In some embodiments, kits are contemplated of use to transport constructs and systems disclosed herein for portable use. In some embodiments, kits can encompass one or more materials needed to perform assays described herein. In accordance with these embodiments, assays disclosed herein can be adapted to one or more portable diagnostic systems. In some embodiments, kits can encompass one or more materials needed to perform assays described herein adapted for a hand-held device for detection of presence and/or concentration of an agent or component of a sample. In certain embodiments, a hand-held device capable of illuminating reaction tubes to detect the fluorescent signal is contemplated herein. In some embodiments, fluorescent probes can be visualized through a yellow plastic film. In certain embodiments, concentration of labeled RNA can be increased to make the fluorescence signal easily visible to the human eye. In accordance with these embodiments, assays herein can use one or more constructs having a fluoride riboswitch to allow for different fluoride concentrations to be differentiated by visual detection by an observer over a period of reaction time. In some embodiments, portable devices contemplated herein can be used by trained personnel to test a sample from a subject for the presence and concentration of a target agent using compositions and methods disclosed herein.

In other embodiments, an agent-responsive component (e.g., zinc responsive factor) can be included in constructs disclosed herein to detect presence or concentration of an agent in a sample (e.g., from a subject and/or in water such as an environmental sample) and presence and/or concentration can be detected using an illuminator device. In accordance with these embodiments, the fluorescence of the control samples can be compared with a calibration curve of the agent of interest, wherein concentration of a target agent in the sample can be approximated by visual analysis and/or by machine as desired.

In some embodiments, fluorescence can be assessed with a device. In some other embodiments, fluorescence can be assessed with the human eye.

EXAMPLES

The following examples are included to illustrate various embodiments. It should be appreciated by those of skill in the art that the techniques disclosed in the examples which follow represent techniques discovered to function well in the practice of the claimed methods, compositions and apparatus. However, those of skill in the art should, in light of the present disclosure, appreciate that changes can be made in some embodiments which are disclosed herein and still obtain a like or similar result without departing from the spirit and scope of the present disclosure.

Example 1

Preparation of SPRINT Templates and SPRINT Assays

Preparation of dsDNA templates for transcription reactions. In one exemplary method, sequences encoding DNA transcription templates (also referred to as "SPRINT transcription templates" in these examples) were cloned into plasmids using the homology-based cloning method (CPEC). pUC plasmid backbones were generated via PCR. The backbone used for insertion of the constant regions including the tac promoter and the target transcript was amplified with the oligos "HA_rev" (SEQ ID NO: 10) and "CreateBBnogRNA2" (SEQ ID NO: 9). Sequences of oligonucleotides and plasmids used in these examples are given in Table 1 and Table 3. Regulatory sequences commonly used in the plasmids in these examples are provided in Table 2.

TABLE 1

| Name of oligonucleotide | Sequence | SEQ ID NO: |
|---|---|---|
| InsulatorOligo fwd | GCTAGCCACAGCTAACACCACGTC | 1 |
| ssDNA1_rev | CTTTATGCTTCCGGCTCGTATGTTGTG | 2 |
| CreateSeq_fwd | CTAAGGATGATTTCTGGAATTC | 3 |
| pbuEBB_fwd | ATTTATCAAAACATTTAAGTAAAGGAGTTTG | 4 |
| pbuEBB_rev | AATAGCTATTTAATTTGAATATATTATACGAGCC | 5 |
| CreateSeq_rev | CGCTTCTGCGTTCTG | 6 |
| RiboswitchBB_fwd | GGCCAGTGAATTCGAGCTCG | 7 |
| *e.coli*Prom_rev | GAATATATTATACGAGCCTTATGCATG | 8 |
| CreateBBnogRNA2 | GAAGCTTGGGCCCGAACAAAAAC | 9 |
| HA_rev | AGATCTTTAGAATTCCAGAAATCATC | 10 |
| crRNA1_rev | GATCCTCTAGAAATATGGATTACTTGGTAGG | 11 |
| 5' gen | GGCGGCGAATTCTAATACGACTCACTATAG | 12 |
| metE_fwd | GCATAAGGCTCGTATAATATATTCCAAAAAATTAATAACA TTTTCTCTTATCGAGAGTTG | 13 |
| metE_rev | CTCATGGGAAAGAGGCTTTTTGGCCAGTGAATTCGAG | 14 |

TABLE 2

| Description | Full Sequence | SEQ ID NO: |
|---|---|---|
| tac promoter for *E. coli* RNAP | TTGACAGGCATGCATAAGGCTCGTATAATATATTC | 15 |
| T7 promoter | TAATACGACTCACTATAGG | 16 |
| Cas13a target site | GATCCTCTAGAAATATGGATTACTTGGTAG | 17 |
| crRNA | GATTTAGACTACCCCAAAAACGAAGGGGACTAAAACCTACCAAGTAATCCATATTTCTAGAGGATC | 18 |
| guanine riboswitch (from xpt/pbuE* 6U) (aptamer bolded) | AATTAAATAGCTATTATCACGATTTT**TATAATCGCGTGGATATGGCACGCAAGTTTCTACCGGGCACCGTAAATGTCCGACTA**AAAATCCTGATTACAAAATTTGTTTATGACATTTTTTGTAATCAGGATTTTTATTTATCAAAACATTTAAGTAAAGGAGTTTGTTATGTTTTTTT | 19 |
| Aptamer from guanine riboswitch | **TATAATCGCGTGGATATGGCACGCAAGTTTCTACCGGGCACCGTAAATGTCCGACTA** | 20 |
| FMN riboswitch (aptamer bolded) | AATTAAATAGCTATTATCACGATTTT**CGGGGCAGGGTGGAAATCCCGACCGGCGGTAGTAAAGCACATTTGCTTTAGAGCCCGTGACCCGTGTGCATAAGCACGCGGTGGATTCAGTTTAAGCTGAAGCCGACAGTGAAAGTCTGGATGGGAG**AAAAATCCTGATTACAAAATTTGTTTATGACATTTTTTGTAATCAGGATTTTTATTTATCAAAACATTTAAGTAAAGGAGTTTGTTATGTTTTTTT | 21 |
| Aptamer from FMN riboswitch | **CGGGGCAGGGTGGAAATCCCGACCGGCGGTAGTAAAGCACATTTGCTTTAGAGCCCGTGACCCGTGTGCATAAGCACGCGGTGGATTCAGTTTAAGCTGAAGCCGACAGTGAAAGTCTGGATGGGAG** | 22 |
| SAM riboswitch (from yitJ/pbuE* 6U) (aptamer bolded) | AATTAAATAGCTATTATCACGATTTT**ATCAAGAGAAGCAGAGGGACTGGCCCGACGAAGCTTCAGCAACCGGTGTAATGGCGATCAGCCATGACCAAGGTGCTAAATCCAGCAAGCTCGAACAGCTTGGAAGAT**AAAATCCTGATTACAAAATTTGTTTATGACATTTTTTGTAATCAGGATTTTTATTTATCAAAACATTTAAGTAAAGGAGTTTGTTATGTTTTTTT | 23 |
| Aptamer from SAM riboswitch | **ATCAAGAGAAGCAGAGGGACTGGCCCGACGAAGCTTCAGCAACCGGTGTAATGGCGATCAGCCATGACCAAGGTGCTAAATCCAGCAAGCTCGAACAGCTTGGAAGAT** | 24 |
| Adenine riboswitch (aptamer bolded) | CACTTG**TATAACCTCAATAATATGGTTTGAGGGTGTCTACCAGGAACCGTAAAATCCTGATTA**CAAGCCGTTTTTTCGGCTTGTAATCAGGATTTTTTTT | 25 |
| Aptamer from Adenine riboswitch | **TATAACCTCAATAATATGGTTTGAGGGTGTCTACCAGGAACCGTAAAATCCTGATTA** | 26 |
| Fluoride riboswitch | TAGGCGATGGAGTTCGCCATAAACGCTGCTTAGCTAATGACTCCTACCAGTATCACTACTGGTAGGAGTCTATTTTTTT | 27 |
| SAM riboswitch (from MetE) | CAAAAAATTAATAACATTTTCTCTTATCGAGAGTTGGGCGAGGGATTGGCCTTTTGACCCCAACAGCAACCGACCGTAATACCATTGTGAAATGGGGCGCACTGCTTTTCGCGCCGAGACTGATGTCTCATAAGGCACGGTGCTAATTCCATCAGATTGTGTCTGAGAGATGAGAGAGGCAGTGTTTTACGTAGAAAAGCCTCTTTCTCTCATGGGAAAGAGGCTTTTT | 28 |
| Zinc aTF operator sequence | CACATGAACAGTTATTCAGATA | 29 |
| tetracycline aTF operator sequence | TCCCTATCAGTGATAGAGA | 30 |

TABLE 3

| Description | Full Sequence | SEQ ID NO: |
|---|---|---|
| SPRINT template constant 5' region with tac promoter for *E. coli* RNAP (bolded) | GCTAGCCACAGCTAACACCACGTCGTCCCTATCTGCTGCCCTAGGTCTATGAGTGGTTGCTGGATAAC**TTGACAGGCATGCATAAGGCTCGTATAATATATTC**a | 31 |

TABLE 3-continued

| Description | Full Sequence | SEQ ID NO: |
|---|---|---|
| SPRINT template constant 5' region with T7 promoter (bolded) | CTAAGGATGATTTCTGGAATTCTAAAGATCT**TAATACGAC TCACTATAGG**GA | 32 |
| SPRINT template constant 3' region with sequence for Target RNA (ssRNA1) (bolded) | GGCCAGTGAATTCGAGCTCGGTACCCGGG**GATCCTCTAGA AATATGGATTACTTGGTAG**AACAGCAATCTACTCGACCTG CAGGCATGCAAGCTTGGCGTAATCATGGTCATAGCTGTTT CCTGTGTTTATCCGCTCACAATTCCACACAACATACGAGC CGGAAGCATAAAG | 33 |
| pUC plasmid containing the sequence for a SPRINT template with the xpt/pbuE*6U riboswitch | gcgagttacatgatcccccatgttgtgcaaaaaagcggtt agctccttcggtcctccgatcgttgtcagaagtaagttgg ccgcagtgttatcactcatggttatggcagcactgcataa ttctcttactgtcatgccatccgtaagatgcttttctgtg actggtgagtactcaaccaagtcattctgagaatagtgta tgcggcgaccgagttgctcttgcccggcgtcaatacggga taataccgcgccacatagcagaactttaaaagtgctcatc attggaaaacgttcttcggggcgaaaactctcaaggatct taccgctgttgagatccagttcgatgtaacccactcgtgc acccaactgatcttcagcatcttttactttcaccagcgtt tctgggtgagcaaaaacaggaaggcaaaatgccgcaaaaa agggaataagggcgacacggaaatgttgaatactcatact cttcctttttcaatattattgaagcatttatcagggttat tgtctcatgagcggatacatatttgaatgtatttagaaaa ataaacaaataggggttccgcgcacatttccccgaaaagt gccacctgacgtctaagaaaccattattatcatgacatta acctataaaaataggcgtatcacgaggcagaatttcagat aaaaaaaatccttagctttcgctaaggatgatttctggaa ttctaaagatctgcgctagccacagctaacacCACGTCGT CCCTATCTGCTGCCCTAGGTCTATGAGTGGTTGCTGGATA ACTTGACAGGCATGCATAAGGCTCGTATAATATATTCaAA TTAAATAGCTATTATCACGATTTTTATAATCGCGTGGATA TGGCACGCAAGTTTCTACCGGGCACCGTAAATGTCCGACT AAAAATCCTGATTACAAAATTTGTTTATGACATTTTTTGT AATCAGGATTTTTTATTTATCAAAACATTTAAGTAAAGGA GTTTGTTATGTTTTTTTTGGCCAGTGAATTCGAGCTCGGT ACCCGGGGATCCTCTAGAAATATGGATTACTTGGtAGAAC AGCAATCTACTCGACCTGCAGGCATGCAAGCTTGGCGTAA TCATGGTCATAGCTGTTTCCTGTGTTTATCCGCTCACAAT TCCACACAACATACGAGCCGGAAGCATAAAGGAAGCTTGG GCCCGAACAAAAACTCatctcagaagaggatctgaatagc gccgtcgaccatcatcatcatcatcattgagtttaaacgg tctccagcttggctgttttggcggatgagagaagattttc agcctgatacagattaaatcagaacgcagaagcggtctga taaaacagaatttgcctggcggcagtagcgcggtggtccc acctgaccccatgccgaactcagaagtgaaacgccgtagc gccgatggtagtgtggggtctccccatgcgagagtaggga actgccaggcatcaaataaaacgaaaggctcagtcgaaag actGGGCCTTTCGTTTTATCTGTTGTTTGTCGGTGAACTG GATCCTTACTCGAGTCTAGACTGCAGgcttcctcgctcac tgactcgctgcgctcggtcgttcggctgcggcgagcggta tcagctcactcaaaggcggtaatacggttatccacagaat caggggataacgcaggaaagaacatgtgagcaaaaggcca gcaaaaggccaggaaccgtaaaaaggccgcgttgctggcg tttttccataggctccgcccccctgacgagcatcacaaaa atcgacgctcaagtcagaggtggcgaaacccgacaggact ataaagataccaggcgtttccccctggaagctccctcgtg cgctctcctgttccgaccctgccgcttaccggatacctgt ccgcctttctcccttcgggaagcgtggcgctttctcatag ctcacgctgtaggtatctcagttcggtgtaggtcgttcgc tccaagctgggctgtgtgcacgaaccccccgttcagcccg accgctgcgccttatccggtaactatcgtcttgagtccaa cccggtaagacacgacttatcgccactggcagcagccact ggtaacaggattagcagagcgaggtatgtaggcggtgcta cagagttcttgaagtggtggcctaactacggctacactag aaggacagtatttggtatctgcgctctgctgaagccagtt accttcggaaaaagagttggtagctcttgatccggcaaac aaaccaccgctggtagcggtggtttttttgtttgcaagca gcagattacgcgcagaaaaaaaggatctcaagaagatcct ttgatcttttctacggggtctgacgctcagtggaacgaaa actcacgttaagggattttggtcatgagattatcaaaaag gatcttcacctagatccttttaaattaaaaatgaagtttt aaatcaatctaaagtatatatgagtaaacttggtctgaca gttaccaatgcttaatcagtgaggcacctatctcagcgat ctgtctatttcgttcatccatagttgcctgactccccgtc gtgtagataactacgatacgggagggcttaccatctggcc ccagtgctgcaatgataccgcgagacccacgctcaccggc | 34 |

TABLE 3-continued

| Description | Full Sequence | SEQ ID NO: |
|---|---|---|
| | tccagatttatcagcaataaaccagccagccggaagggcc<br>gagcgcagaagtggtcctgcaactttatccgcctccatcc<br>agtctattaattgttgccgggaagctagagtaagtagttc<br>gccagttaatagtttgcgcaacgttgttgccattgctaca<br>ggcatcgtggtgtcacgctcgtcgtttggtatggcttcat<br>tcagctccggttcccaacgatcaag | |
| DNA template for transcription of crRNA against ssRNA1<br>tac promoter bolded<br>crRNA against SsRNA1 underlined | **GGCGGCGAATTCTAATACGACTCACTATAG**GGGAAGATTT<br>AGACTACCCCAAAAACGAAGGGGACTAAAACCTACCAAGT<br>AATCCATATTTCTAGAGGATC | 35 |
| none (constitutive tac promoter)<br>tac promoter bolded<br>Cas13a target site underlined | GCTAGCCACAGCTAACACCACGTCGTCCCTATCTGCTGCC<br>CTAGGTCTATGAGTGGTTGCTGGATAAC**TTGACAGGCATG**<br>**CATAAGGCTCGTATAATATATTC**GGCCAGTGAATTCGAGC<br>TCGGTACCCGGGGATCCTCTAGAAATATGGATTACTTGgt<br>AGAACAGCAATCTACTCGACCTGCAGGCATGCAAGCTTGG<br>CGTAATCATGGTCATAGCTGTTTCCTGTGTTTATCCGCTC<br>ACAATTCCACACAACATACGAGCCGGAAGCATAAAG | 36 |
| xpt/pbuE* 6U<br>(guanine riboswitch)<br>tac promoter italicized<br>riboswitch underlined<br>aptamer bolded<br>Cas13a target site underlined and italicized | GCTAGCCACAGCTAACACCACGTCGTCCCTATCTGCTGCC<br>CTAGGTCTATGAGTGGTTGCTGGATAAC*TTGACAGGCATG*<br>*CATAAGGCTCGTATAATATATTC*aAATTAAATAGCTATTA<br>TCACGATTTT**TATAATCGCGTGGATATGGCACGCAAGTTT**<br>**CTACCGGGCACCGTAAATGTCCGACTA**AAAATCCTGATTA<br>CAAAATTTGTTTATGACATTTTTTGTAATCAGGATTTTTT<br>ATTTATCAAAACATTTAAGTAAAGGAGTTTGTTATGTTTT<br>TTTTGGCCAGTGAATTCGAGCTCGGTACCCGGG*GATCCTC*<br>*TAGAAATATGGATTACTTGgtAG*AACAGCAATCTACTCGA<br>CCTGCAGGCATGCAAGCTTGGCGTAATCATGGTCATAGCT<br>GTTTCCTGTGTTTATCCGCTCACAATTCCACACAACATAC<br>GAGCCGGAAGCATAAAG | 37 |
| ribD/pbuE* 7U<br>(FMN riboswitch)<br>tac promoter italicized<br>riboswitch underlined<br>aptamer bolded<br>Cas13a target site underlined and italicized | GCTAGCCACAGCTAACACCACGTCGTCCCTATCTGCTGCC<br>CTAGGTCTATGAGTGGTTGCTGGATAAC*TTGACAGGCATG*<br>*CATAAGGCTCGTATAATATATTC*aAATTAAATAGCTATTA<br>TCACGATTTT**CGGGGCAGGGTGGAAATCCCGACCGGCGG**<br>**TAGTAAAGCACATTTGCTTTAGAGCCCGTGACCCGTGTGC**<br>**ATAAGCACGCGGTGGATTCAGTTTAAGCTGAAGCCGACAG**<br>**TGAAAGTCTGGATGGGAG**AAAAATCCTGATTACAAAATTT<br>GTTTATGACATTTTTTGTAATCAGGATTTTTTATTTATC<br>AAAACATTTAAGTAAAGGAGTTTGTTATGTTTTTTTTGGC<br>CAGTGAATTCGAGCTCGGTACCCGGG*GATCCTCTAGAAAT*<br>*ATGGATTACTTGgtAG*AACAGCAATCTACTCGACCTGCAG<br>GCATGCAAGCTTGGCGTAATCATGGTCATAGCTGTTTCCT<br>GTGTTTATCCGCTCACAATTCCACACAACATACGAGCCGG<br>AAGCATAAAG | 38 |
| yitJ/pbuE* 6U<br>(SAM riboswitch)<br>tac promoter italicized<br>riboswitch underlined<br>aptamer bolded<br>Cas13a target site underlined and italicized | GCTAGCCACAGCTAACACCACGTCGTCCCTATCTGCTGCC<br>CTAGGTCTATGAGTGGTTGCTGGATAAC*TTGACAGGCATG*<br>*CATAAGGCTCGTATAATATATTC*aAATTAAATAGCTATTA<br>TCACGATTTT**ATCAAGAGAAGCAGAGGGACTGGCCCGACG**<br>**AAGCTTCAGCAACCGGTGTAATGGCGATCAGCCATGACCA**<br>**AGGTGCTAAATCCAGCAAGCTCGAACAGCTTGGAAGAT**AA<br>AATCCTGATTACAAAATTTGTTTATGACATTTTTTGTAAT<br>CAGGATTTTTTATTTATCAAAACATTTAAGTAAAGGAGTT<br>TGTTATGTTTTTTTTGGCCAGTGAATTCGAGCTCGGTACC<br>CGGG*GATCCTCTAGAAATATGGATTACTTGgtAG*AACAGC<br>AATCTACTCGACCTGCAGGCATGCAAGCTTGGCGTAATCA<br>TGGTCATAGCTGTTTCCTGTGTTTATCCGCTCACAATTCC<br>ACACAACATACGAGCCGGAAGCATAAAG | 39 |
| pbuE/pbuE<br>(adenine riboswitch)<br>tac promoter italicized<br>riboswitch underlined<br>aptamer bolded and underlined<br>Cas13a target site underlined and italicized | GCTAGCCACAGCTAACACCACGTCGTCCCTATCTGCTGCC<br>CTAGGTCTATGAGTGGTTGCTGGATAAC*TTGACAGGCATG*<br>*CATAAGGCTCGTATAATATATTC*aCACTTG**TATAACCTCA**<br>**ATAATATGGTTTGAGGGTGTCTACCAGGAACCGTAAAATC**<br>**CTGATTA**CAAGCCGTTTTTTCGGCTTGTAATCAGGATTTT<br>TTTTGGCCAGTGAATTCGAGCTCGGTACCCGGG*GATCCTC*<br>*TAGAAATATGGATTACTTGgtAG*AACAGCAATCTACTCGA<br>CCTGCAGGCATGCAAGCTTGGCGTAATCATGGTCATAGCT<br>GTTTCCTGTGTTTATCCGCTCACAATTCCACACAACATAC<br>GAGCCGGAAGCATAAAG | 40 |
| crcB (fluoride riboswitch)<br>tac promoter italicized<br>riboswitch underlined | GCTAGCCACAGCTAACACCACGTCGTCCCTATCTGCTGCC<br>CTAGGTCTATGAGTGGTTGCTGGATAAC*TTGACAGGCATG*<br>*CATAAGGCTCGTATAATATATTC*TAGGCGATGGAGTTCGC | 41 |

TABLE 3-continued

| Description | Full Sequence | SEQ ID NO: |
|---|---|---|
| Cas13a target site underlined<br>and italicized | CATAAACGCTGCTTAGCTAATGACTCCTACCAGTATCACT<br>ACTGGTAGGAGTCTATTTTTTTGGCCAGTGAATTCGAGCT<br>CGGTACCCGGG*GATCCTCTAGAAATATGGATTACTTGGTA*<br>*G*AACAGCAATCTACTCGACCTGCAGGCATGCAAGCTTGGC<br>GTAATCATGGTCATAGCTGTTTCCTGTGTTTATCCGCTCA<br>CAATTCCACACAACATACGAGCCGGAAGCATAAAG | |
| metE (SAM riboswitch)<br>tac promoter italicized<br>riboswitch underlined<br>Cas13a target site underlined<br>and italicized | GCTAGCCACAGCTAACACCACGTCGTCCCTATCTGCTGCC<br>CTAGGTCTATGAGTGGTTGCTGGATAAC*TTGACAGGCATG*<br>*CATAAGGCTCGTATAATATATTC*CAAAAAATTAATAACAT<br>TTTCTCTTATCGAGAGTTGGGCGAGGGATTGGCCTTTTGA<br>CCCCAACAGCAACCGACCGTAATACCATTGTGAAATGGGG<br>CGCACTGCTTTTCGCGCCGAGACTGATGTCTCATAAGGCA<br>CGGTGCTAATTCCATCAGATTGTGTCTGAGAGATGAGAGA<br>GGCAGTGTTTTACGTAGAAAAGCCTCTTTCTCTCATGGGA<br>AAGAGGCTTTTTGGCCAGTGAATTCGAGCTCGGTACCCGG<br>G*GATCCTCTAGAAATATGGATTACTTGGTAG*AACAGCAAT<br>CTACTCGACCTGCAGGCATGCAAGCTTGGCGTAATCATGG<br>TCATAGCTGTTTCCTGTGTTTATCCGCTCACAATTCCACA<br>CAACATACGAGCCGGAAGCATAAAG | 42 |
| none (constitutive T7 promoter)<br>T7 promoter bolded<br>Cas13a target site underlined | CTAAGGATGATTTCTGGAATTCTAAAGATCT**TAATACGAC**<br>**TCACTATAGG**GGCCAGTGAATTCGAGCTCGGTACCCGGGG<br>ATCCTCTAGAAATATGGATTACTTGGTAGAACAGCAATCT<br>ACTCGACCTGCAGGCATGCAAGCTTGGCGTAATCATGGTC<br>ATAGCTGTTTCCTGTGTTTATCCGCTCACAATTCCACACA<br>ACATACGAGCCGGAAGCATAAAG | 43 |
| Zinc aTF smtB<br>T7 promoter italicized<br>aTF operator sequence<br>bolded<br>Cas13a target site underlined | CTAAGGATGATTTCTGGAATTCTAAAGATCT*TAATACGAC*<br>*TCACTATAGG*GA**CACATGAACAGTTATTCAGATA**GGCCAG<br>TGAATTCGAGCTCGGTACCCGGGGATCCTCTAGAAATATG<br>GATTACTTGGTAGAACAGCAATCTACTCGACCTGCAGGCA<br>TGCAAGCTTGGCGTAATCATGGTCATAGCTGTTTCCTGTG<br>TTTATCCGCTCACAATTCCACACAACATACGAGCCGGAAG<br>CATAAAG | 44 |
| tetracycline aTF tetR<br>T7 promoter italicized<br>aTF operator sequence<br>bolded<br>Cast 3a target site underlined | CTAAGGATGATTTCTGGAATTCTAAAGATCT*TAATACGAC*<br>*TCACTATAGG*GA**TCCCTATCAGTGATAGAGA**GGCCAGTGA<br>ATTCGAGCTCGGTACCCGGGGATCCTCTAGAAATATGGAT<br>TACTTGGTAGAACAGCAATCTACTCGACCTGCAGGCATGC<br>AAGCTTGGCGTAATCATGGTCATAGCTGTTTCCTGTGTTT<br>ATCCGCTCACAATTCCACACAACATACGAGCCGGAAGCAT<br>AAAG | 45 |

When generating backbones for the purpose of exchanging riboswitches within the constant regions of the SPRINT template, the oligos "e.coliProm_rev" (SEQ ID NO: 8) and "RiboswitchBB_fwd" (SEQ ID NO: 7) were used. In cases when aptamer domains of the pbuE*6U expression platform were exchanged, the backbone was amplified with the oligonucleotides "pbuEBB_rev" (SEQ ID NO: 5) and "pbuEBB_fwd" (SEQ ID NO: 4). All plasmids were sequence-verified.

dsDNA SPRINT transcription templates were amplified for use in assays from plasmids via PCR unless stated otherwise. The oligonucleotides used for PCR to amplify templates with riboswitches were "InsulatorOligo_fwd" (SEQ ID NO: 1) and "ssDNA1_rev" (SEQ ID NO: 2). Templates that contained operator sequences for aTF binding instead of riboswitches were amplified with the oligos "CreateSeq_fwd" (SEQ ID NO: 3) and "ssDNA1_rev" (SEQ ID NO: 2).

For amplification of the native metE riboswitch from the genome, the following protocol was used: Colony PCR was performed, using the oligos "metE_fwd" (SEQ ID NO: 13) and "metE_rev" (SEQ ID NO: 14) at $T_m$=64° C. with Q5 DNA polymerase. The constant 5' and 3' parts of the SPRINT constructs were also amplified via PCR reactions, using any plasmid with a complete SPRINT sequence as template. The 5' constant part was amplified with oligos "InsulatorOligo_fwd" (SEQ ID NO:1) and "e.coliProm_rev" (SEQ ID NO: 8). The 3' constant part was amplified with oligos "RiboswitchBB_fwd" (SEQ ID NO: 7) and "ssDNA1_rev" (SEQ ID NO: 2). The three pieces (5', metE riboswitch, 3') were assembled and amplified in a single PCR reaction: 5 nM each of the 5' region, the metE region, and the 3' region and 500 nM each of the oligos "InsulatorOligo_fwd" (SEQ ID NO: 1) and "ssDNA1_rev" (SEQ ID NO: 2) were added to a PCR reaction with the Q5 DNA polymerase. 5 amplification cycles were run at $T_m$=61° C. to assemble the three pieces and then 25 cycles were run at 70° C. to amplify the assembled construct with the oligos. The PCR product was purified, quantified and used for a SPRINT reaction.

In Vitro Transcription and Purification of RNA with T7 RNAP.

The crRNA and the ssRNA1 were transcribed in vitro and purified. DNA template for in vitro transcription was amplified in a 200 μL PCR reaction using the oligos "5' gen" (SEQ ID NO: 12) and "crRNA1_rev" (SEQ ID NO: 11). RNA was synthesized in a 2.5 mL transcription reaction containing 200 μL unpurified PCR reaction in T7 transcription buffer. 1× transcription buffer contains the following reagents: 40 mM Tris-HCl, pH 8.0, 10 mM DTT, 8 mM $MgCl_2$, 2 mM spermidine, 0.01% (v/v) Triton X-100. ATP, GTP, CTP and UTP were added to a final concentration of 4 mM each, inorganic pyrophosphatase (IPPase) was added to 160 milliUnits/μL and T7 RNA polymerase was added to 320 nM. The reaction was incubated at 37° C. for 2 hours, followed by addition of 3 mL 100% ethanol to the reaction and precipitation of the RNA at −80° C. for 1 hour. The reaction was centrifuged at 4,000×g at 4° C. for 15 minutes. The supernatant was discarded and the pellet was air-dried at 37° C. for 3 hours and then re-suspended in 1 mL of 8 M urea, 500 μL 0.5 M EDTA, pH 8.0, and 1 mL of formamide loading dye (0.025% (w/v) bromophenol blue, 5 mM EDTA, pH 8.0, 0.025% (w/v) SDS dissolved in formamide). Transcripts were separated by electrophoresis using a denaturing polyacrylamide gel (10% 29:1 acrylamide/bisacrylamide, 1×TBE buffer (0.1 M Tris base, 80 mM boric acid, 1 mM $Na_2EDTA$), and 8 M urea) and the RNA bands were visualized by UV shadowing. The correct length transcript was excised from the gel and the RNA extracted into 0.5× TE reagent buffer (5 mM Tris-HCl, pH 8.0, 250 μM EDTA) by gentle agitation at 4° C. overnight. The mixture was centrifuged at 4,000×g for 30 minutes and RNA from the supernatant was concentrated to approximately 1 mL each using centrifugal concentrators with a 10 kDa molecular weight cutoff (0.5 mL) and buffer exchanged into 0.5× TE reagent buffer. The concentrate was passed through a large-pored Sepharose filter to remove remaining gel pieces. The concentration of RNAs was determined by their absorbance at 260 nm, and stored as concentrated stocks at −80° C. Prior to use, the crRNA was diluted to 2.25 μM and the target RNA as 1 μM-1 nM aliquots, which were stored at −20° C.

Purification of LwaCas13a Protein.

LwaCas13a from *Leptotrichia wadeii* has a specific preference for collaterally cleaving poly-uracil ssRNA oligos and was used for various experiments in these examples. LwaCas13a was purified as follows. The expression plasmid (pC013) encoded LwaCas13a with an N-terminal His-tag, followed by twinstrep and SUMO tags. The plasmid was transformed into BL21(DE3) Rosetta *Escherichia coli* cells. 20 mL bacterial culture was grown overnight in Luria broth (LB) medium supplemented with 100 μM carbenicillin that was used to inoculate 1 L cultures in LB medium. The culture was shaken at 37° C. until the $OD_{600}$ reached around 0.6. The culture was cooled down to approximately 20° C. in a cold water bath and protein expression was induced by adding 0.5 mM Isopropyl beta-D-1-thiogalactopyronoside (IPTG). The culture was grown in a 20° C. shaker for 16 hours. Bacterial cells were pelleted at 4,000×g at 4° C. for 30 minutes and the cell pellets resuspended in lysis reagent buffer (0.5 M NaCl, 20 mM Tris-HCl, pH 8.0, and 1 mM DTT). All subsequent purification steps were carried out at 4° C. Cells were lysed using an Emulsiflex C3 homogenizer and cell debris pelleted by centrifugation at 17,000×g for 30 minutes. Polyethyleneimine (PEI) was used to precipitate the nucleic acid contaminants. The supernatant (~35 mL) was stirred rapidly while 250 μL 5% PEI was slowly added carefully. The supernatant was stirred for 15 more minutes and then centrifuged at 12,000×g for 20 minutes to pellet the precipitate. Then, the supernatant was incubated with Ni-NTA sepharose beads on an orbital shaker for 1 hour at 4° C. Beads were centrifuged at 300×g for 2 minutes and washed 15 minutes with 40 mL lysis reagent buffer containing 10 mM imidazole in the first wash, 50 mM imidazole in the second wash and finally elution with 250 mM imidazole. 1 mL of SUMO protease was added to the eluate and incubated at 4° C. for 16 hours while gently shaking. Then, the protein was incubated with Ni-NTA beads again to bind any uncleaved protein and subsequently concentrated in S200 buffer (10 mM HEPES, 1 M NaCl, 5 mM $MgCl_2$, 2 mM DTT, pH 7.0) Size exclusion purification was conducted on a Hiload 16/600 Superdex 200 column in S200 buffer. The Cas13a-containing fractions were pooled, concentrated to approximately 2 mL and the buffer was exchanged to Cas13 storage reagent buffer (50 mM Tris-HCl, pH 7.5, 600 mM NaCl, 5% glycerol, 2 mM DTT). Protein concentration was determined using the absorbance at 280 nm and an extinction coefficient of 119800 $M^{-1}$ $cm^{-1}$; 1.5 mL of 47 μM protein was obtained from 2 liters of culture. Aliquots were diluted to 4.5 μM for use and stored at −20° C. while the concentrated stock was stored at −80° C.

SPRINT Reactions.

Pentauridine RNA oligonucleotides were labeled with carboxyfluorescein (FAM) or TEX 615 at the 5'-end and with Iowa Black FQ at the 3'-end. Fluorescence measurements were taken at wavelengths 490/525 nm (excitation/emission) when the FAM fluorophore was used. In reactions with flavin-containing ligands, TEX-labeled RNA oligos were used at the wavelengths 576/615 (excitation/emission). Fluorescence measurements were taken every 5 minutes.

For exemplary SPRINT assays, a master mix was first prepared and then mixed with the remaining reaction reagent components to yield a final reaction volume of 30 μL; fluorescent readings of the entire reaction volume were performed in Corning 384 Flat Bottom Black Polystyrol plates. This master mix (SPRINT buffer, 10×), for assays contemplated herein can include, but is not limited to: 700 mM Tris-HCl, pH 8.0, 700 mM NaCl, 1 mM EDTA, 140 mM β-mercaptoethanol, and 25 mM $MgCl_2$. Aliquots of an exemplary 10×SPRINT buffer were stored at −20° C. and not allowed to undergo more than 10 freeze-thaw cycles.

For exemplary riboswitch-regulated reactions, master mix reagents were added in this order: water, 1×SPRINT buffer, 0.4 U/μL murine RNase Inhibitor, 2.5 nM dsDNA template, 22.5 nM crRNA, 125 nM $U_5$-RNA oligos, 45 nM Cas13a, 0.01 U/μL *E. coli* RNAP Holoenzyme. The master mix was gently mixed by pipetting up and down and incubated at 37° C. for 15 minutes to allow binding of crRNA to Cas13a protein and the microwell plate was prepared by adding 3 μL of 10× ligand to the wells. The reaction was initiated by addition of rNTPs to the master mix to a concentration of 20 μM and then 27 μL of the complete master mix were added to each well and pipetted up and down to mix with the ligand in the wells. The plate was covered with an optical adhesive film to prevent evaporation of the sample while taking fluorescence measurements in a plate reader that was preheated to 37° C.

In other exemplary methods, reactions with allosteric transcription factors (aTFs), ROSALIND reagent buffer (10× buffer containing, for assays contemplated herein, but not limited to: 400 mM Tris-HCl, pH 8.0, 200 mM NaCl, 20 mM spermidine, 100 mM DTT and 80 mM $MgCl_2$) were used. The buffer was prepared fresh or stored as single-use aliquots at −80° C. The reagents were added in this order: water, 1× ROSALIND buffer, 0.4 U/μL murine RNase Inhibitor, 15 nM dsDNA template, 22.5 nM crRNA, 125 nM $U_5$-RNA oligos, 45 nM Cas13a, 6.67 ng/μL T7 RNAP and aTF. The final concentration of the aTF monomers was either 2.5 μM tetR or 10 μM smtB. The master mix was incubated for 15 minutes at 37° C. which allows the aTFs to bind to the operator sequence. Then, rNTPs were added to a concentration of 40 μM to initiate the reaction and the master mix was added to each well and pipetted up and down to mix with the ligand in the wells.

For exemplary reactions in the handheld illuminator, reactions were assembled as described above, except that the final concentration of FAM-labeled $U_5$-RNA oligos was increased to 1.25 μM so that the fluorescence could be seen by the human eye. Images were recorded with a digital camera for immediate or later analysis.

In another exemplary method, two-batch methods included, 30 μL in vitro transcription reactions carried out as described above but without addition of Cas13a, crRNA, labeled RNA oligos, RNase inhibitor. Then, the reaction was washed three times with 500 μL $ddH_2O$ using an centrifugal filter (0.5 ml, 10 kDa cutoff). After concentrating the solution to approximately 20 μL, aliquots of 6 μL were taken and added to a 24 μL of a SHERLOCK reaction (described below).

In other methods, SHERLOCK reactions were performed with purified target RNA as input, the concentration of the components, order of addition of components and measurement of fluorescence was carried out the same way as in the SPRINT reactions. This master mix (SHERLOCK buffer, 10×), for assays contemplated herein can include, but is not limited to: 200 mM HEPES, pH 6.8, 600 mM NaCl, 60 mM $MgCl_2$ Sequences encoding SPRINT transcription templates were cloned into plasmids using the homology-based cloning method (CPEC). pUC plasmid backbones were generated via PCR. The backbone used for insertion of the constant regions including the tac promoter and the target transcript was amplified with the oligos "HA_rev" (SEQ ID NO:10) and "CreateBBnogRNA2" (SEQ ID NO: 9). Sequences of plasmids and oligonucleotides used in these examples are provided in Tables 1 and 2.

Example 2

Optimization and Benchmark of SPRINT

Figures 2A, 2B, 2C, 2D, 2E:
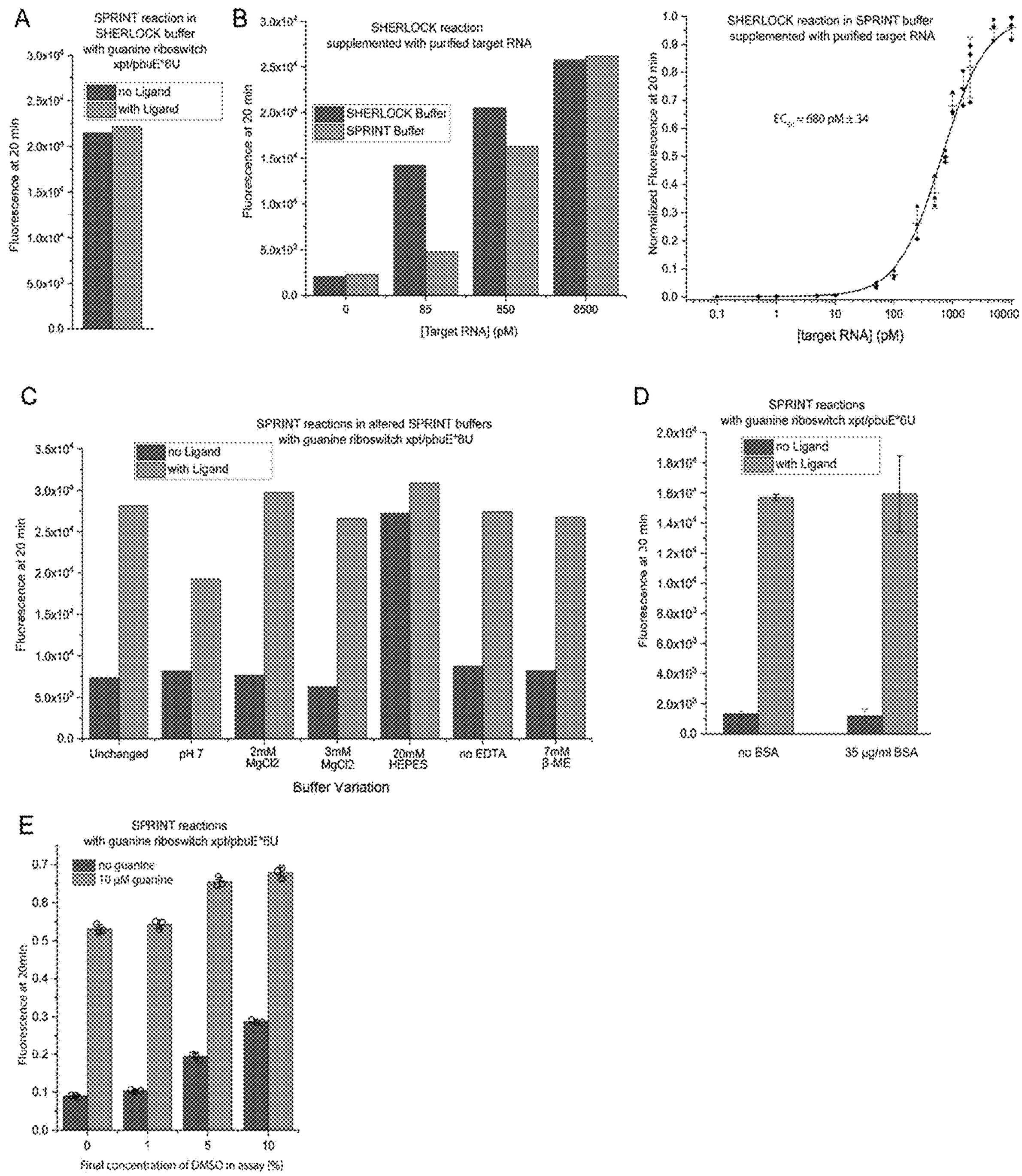
FIGS. 2A-2E illustrate exemplary histogram plots and a graph (2A-2E) of fluorescence recorded from exemplary transcription reactions in exemplary assays disclosed herein in accordance with certain embodiments of the present disclosure.

In another exemplary method, to couple RNA polymerase-driven in vitro transcription and Cas13a-mediated RNA cleavage, assay conditions were established to enable a single combined reaction. Initially, the reagent components needed for transcription of the synthetic guanine-responsive riboswitch xpt/pbuE*6U were added to the SHERLOCK reaction using a 1× dilution of the standard SHERLOCK buffer described in the example above. In the absence of guanine, this riboswitch formed an intrinsic terminator that caused RNA polymerase to abort synthesis and thereby not synthesize a sequence that was recognized by Cas13a RNP. However, this yielded a high fluorescent signal in the absence of guanine (FIG. 2A). Thus, directly adopting the conditions used for SHERLOCK reaction prevented coupling of ligand-regulated transcription and Cas13a-mediated cleavage.

It was next tested whether Cas13a could function in a buffer reagent system designed to promote efficient riboswitch-mediated transcriptional termination. This buffer system, referred to herein as a SPRINT buffer, generally was prepared from a 10×SPRINT buffer described above (700 mM Tris-HCl, pH 8.0, 700 mM NaCl, 1 mM EDTA, 140 mM β-mercaptoethanol, and 25 mM $MgCl_2$) and optimized as described herein. To determine if Cas13a was capable of cleaving RNA in SPRINT buffer, purified target RNA was added to the reaction to activate Cas13a. Target RNA could be detected by Cas13a in both SHERLOCK and SPRINT buffer systems, although with slightly different dose-responses (FIG. 2B). Thus, the response of Cas to a series of target RNA concentrations was measured in the SPRINT buffer system and it was shown that RNA concentrations in the range of 10 pM to 10 nM could be quantified (FIG. 2B). In certain methods, altering various factors such as pH, magnesium concentration, or the inclusion of HEPES, EDTA or beta-mercaptoethanol in the SPRINT buffer composition resulted either in no change or a decrease in detection of guanine-induced read-through transcription (FIG. 2C). As BSA did not improve the assay in these examples, it was removed from the reagent buffer (FIG. 2D) to decrease the risk of RNase contamination from protein preparations. Since many hydrophobic small molecule compounds cannot be dissolved in water but in DMSO, the response of SPRINT reactions was also measured in increasing amounts of DMSO (FIG. 2E). Although DMSO slightly increased both background and on-signal, final concentrations of 10% DMSO did not inhibit the assay.

Figures 3A, 3B, 3C, 3D:
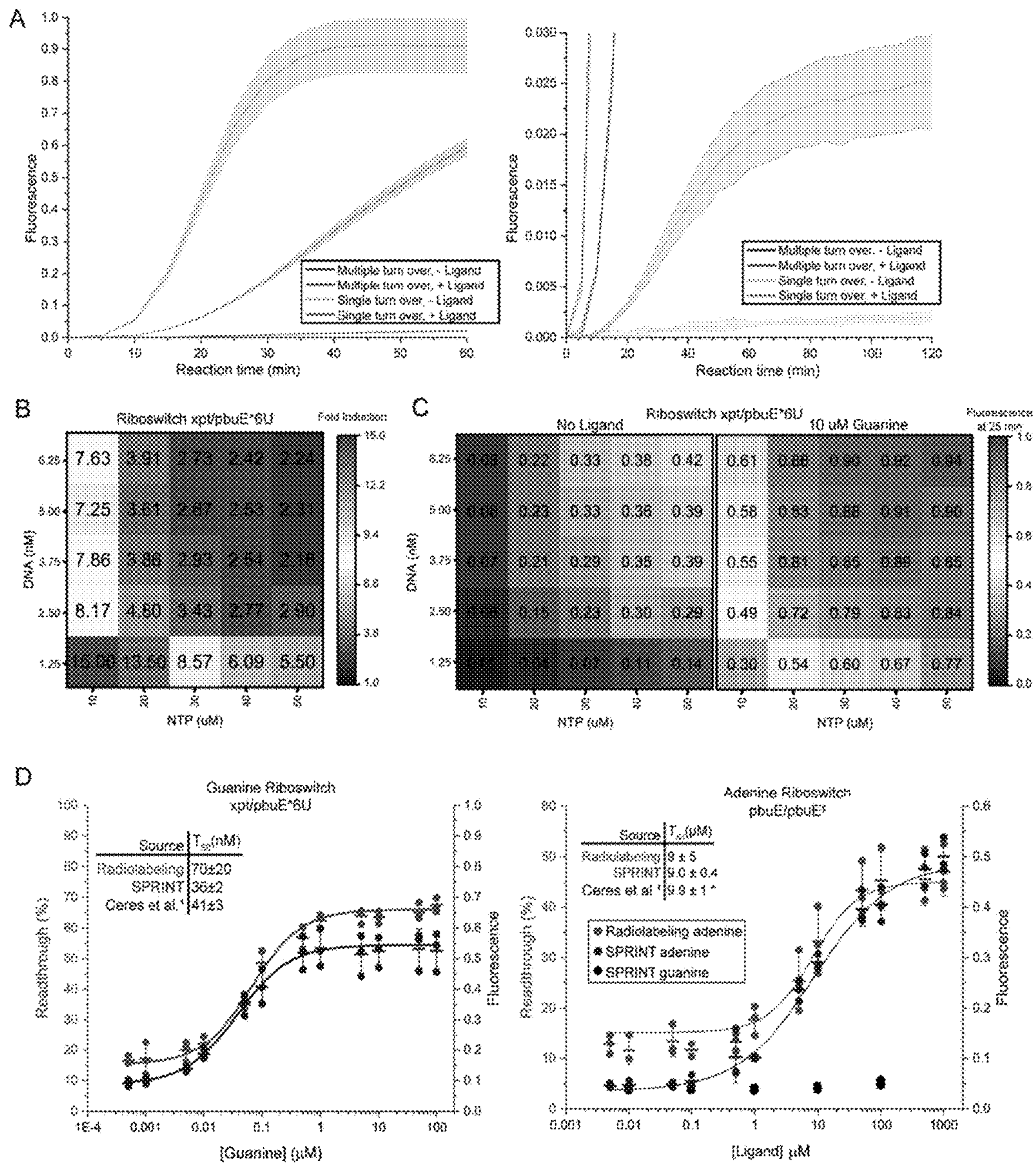
FIG. 3A represent exemplary plots of fluorescence detected in single turnover assays (STA) with heparin or multiple turnover assays (MTA) without heparin performed using a guanine activated riboswitch in the presence or absence of its cognate ligand and as measured by an exemplary assay disclosed herein in accordance with certain embodiments of the present disclosure.
FIGS. 3B-3C represent exemplary heatmaps demonstrating relative levels of transcription induced by a guanine activated riboswitch in the presence or absence of its cognate ligand and as measured by an exemplary assay disclosed herein in accordance with certain embodiments of the present disclosure.
FIG. 3D represent exemplary histogram plots demonstrating activity of two different riboswitches in the presence of their cognate ligands as measured by an exemplary assay disclosed herein or using a control standard method in accordance with certain embodiments of the present disclosure.

To assess the fluorescent signal arising from single- and multiple-turnover transcription, SPRINT assays with the xpt/pbuE*6U guanine riboswitch were tested with and without heparin (FIG. 3A). Repression of fluorescent signal in the absence of ligand was more efficient in the single turnover assays with heparin, but the signal in the multiple-turnover assays was approximately 35-fold larger and reached its maximum approximately twice as fast. This shows that, in certain instances, multiple turn over transcriptions were mainly responsible for the strength of the fluorescent signal and not the multiple turn over reactions of the Cas13 enzyme. For this reason, most SPRINT assays were conducted without heparin but note that SPRINT can be run as a single-turnover assay whenever a minimized background signal was preferred over a fast response. Using the same riboswitch, ligand-dependent signals arising from a range of concentrations of the DNA template and the rNTPs were assessed. The lowest concentrations of DNA and NTP resulted in the largest fold change when the riboswitch was induced with 10 μM guanine (FIG. 3B). However, because these low concentrations led to a slow rise of the fluorescent signal herein (FIG. 3C), subsequent exemplary experiments were designed to achieve a higher fold induction for faster signals using 2.5 nM DNA template and 20 μM NTP.

Next, exemplary studies assessed whether SPRINT results were comparable to results obtained via radiolabeling of RNA—the "gold standard" in quantifying transcription reactions. The transcriptional response of the well-characterized guanine riboswitch xpt/pbuE*6U and the adenine-responsive riboswitch pbuE/pbuE‡ to their respective ligand was measured by SPRINT and the radiolabeling method. The radiolabeling method used $^{32}P$-labeled ATP for single turnover transcription assays, subsequent separation of the transcripts on an acrylamide gel, exposure to a phospho screen and quantification of the band intensities. The $T_{50}$ value, the ligand concentration at half-maximal activation of transcription, was obtained from a fit to the data (FIG. 3D) and used to compare the two methods. For both riboswitches, the $T_{50}$ was similar between SPRINT, radiolabeling and values from the literature that were also obtained with radiolabeling. This indicated that results obtained with SPRINT were comparable to those obtained with radiolabeling while increasing the speed, ease and throughput of transcription assays. Together, these exemplary studies established that small-molecule dependent transcriptional regulation and Cas13a-mediated RNA cleavage can be combined into a single reaction.

Example 3

Adaption of SPRINT to Various Riboswitches

Figures 4A, 4B, 4C, 4D, 4E:
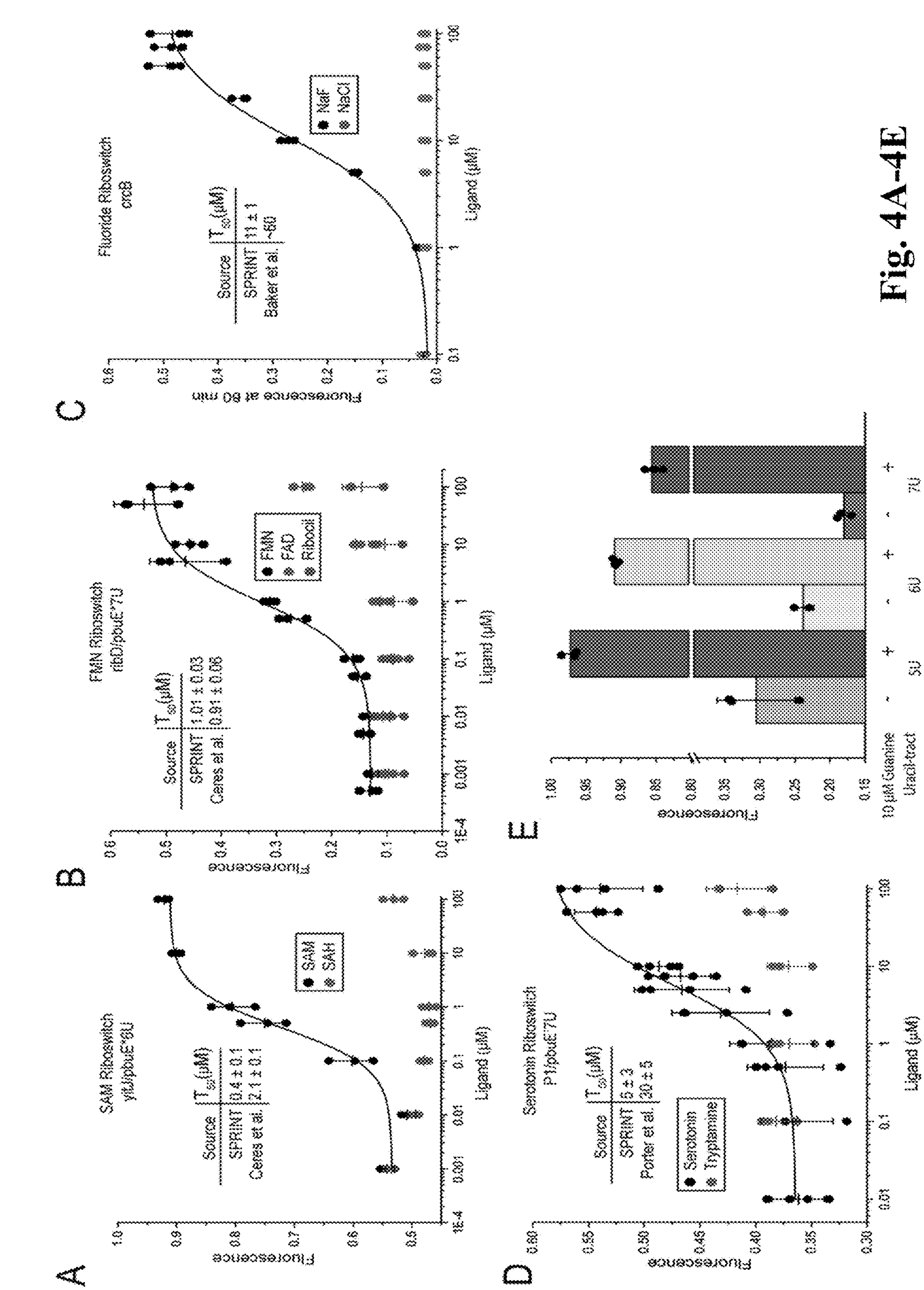
FIGS. 4A-4E illustrate exemplary graphs of representative assays which were used to measure concentrations of agents, with novel double-stranded DNA sequences containing a variety of switches including a (4A) SAM riboswitch, (4B) FMN riboswitch, (4C) fluoride riboswitch, or (4D) serotonin riboswitch, as regulatory elements, in accordance with certain embodiments of the present disclosure. 4E illustrates a histogram plot of exemplary assays measuring three different expression platforms for a guanine riboswitch in accordance with certain embodiments of the present disclosure.

In another exemplary method, to test the versatility of SPRINT, small-molecule dependent transcriptional regulation of various riboswitches was examined. The adenine riboswitch pbuE/pbuE‡ responded efficiently to adenine but not guanine (FIG. 3D). The S-adenosylmethionine (SAM)-responsive riboswitch yitJ/pbuE*6U was responsive to SAM but not to the related compound S-adenosylhomocysteine (SAH); the $T_{50}$ value for SAM was comparable to prior measurements using the $^{32}P$-labeling assay (FIG. 4A). All three riboswitches, xpt/pbuE*6U, pbuE/pbuE‡, and yitJ/pbuE*6U used a version of the pbuE expression platform and the ligand specificity was altered by simply exchanging the aptamer domain.

Figure 5:
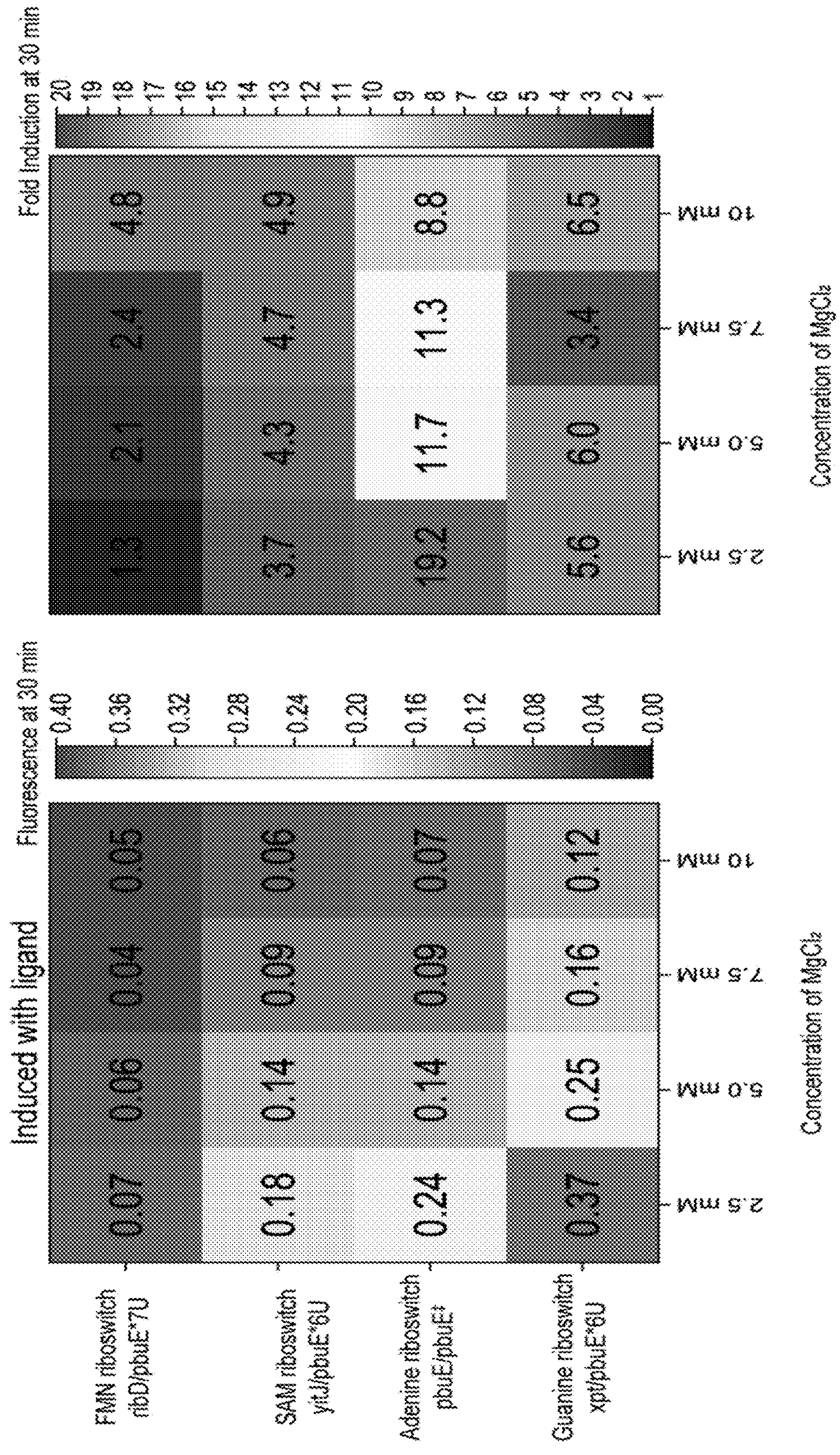
FIG. 5 illustrates an exemplary chart of data from exemplary assays used to measure effect of additives, with various riboswitches: an FMN riboswitch, an SAM riboswitch, an adenine riboswitch, or a guanine riboswitch in accordance with certain embodiments of the present disclosure.

The flavin mononucleotide (FMN) riboswitch ribD/pbuE*7U—derived from the *B. subtilis* ribD riboswitch—exhibited a high-affinity response to FMN with a $T_{50}$ value around 1.01±0.03 μM and a low-affinity response to flavin adenine dinucleotide (FAD) (FIG. 4B). Initially, the observed ligand-dependent induction of the FMN riboswitch was very low. To improve this, the magnesium concentration in the SPRINT reaction was increased. Of the four riboswitches (ribD/pbuE*7U, yitJ/pbuE*6U, pbuE/pbuE‡, xpt/pbuE*6U) that were tested at higher $MgCl_2$ concentrations, only the ribD riboswitch showed a significant increase in fold induction (FIG. 5). Therefore, SPRINT reactions with the ribD/pbuE*7U riboswitch were conducted at 10 mM $MgCl_2$ in these exemplary studies. Interestingly, there was no observable activation of the ribD/pbuE*7U riboswitch by ribocil-C, a synthetic FMN mimic that was a strong agonist of the related FMN riboswitch ribB from *E. coli* and also the FMN riboswitch from *F. nucleatum*. These data supported that ribocil specifically bound to the FMN binding pocket in the riboswitches from *E. coli* and *F. nucleatum* but showed reduced affinity to other FMN riboswitches with differing sequence.

Figures 6A, 6B, 6C, 6D, 6E, 6F:
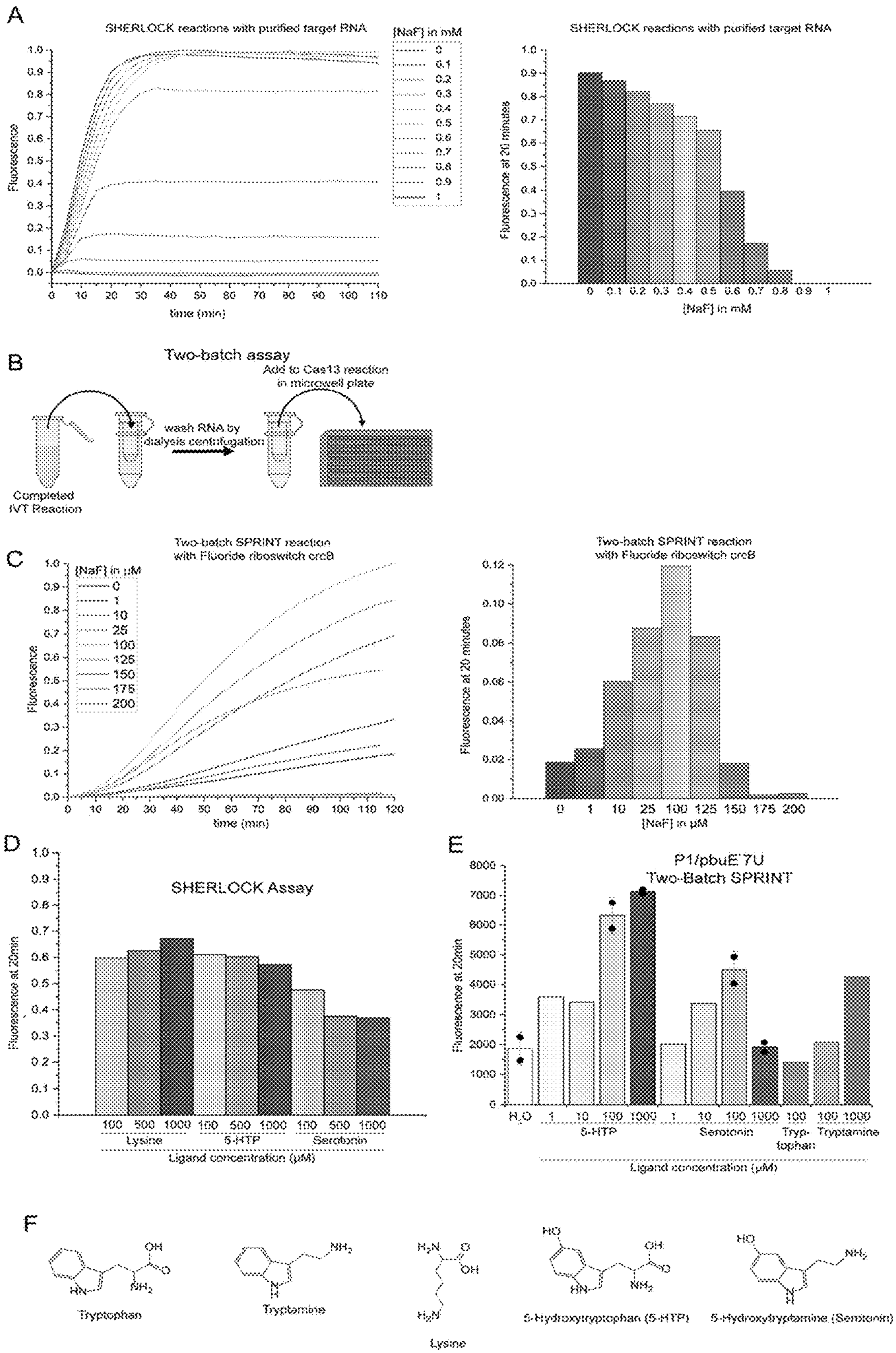
FIG. 6A represents an exemplary graph and histogram plot depicting data from an exemplary assay to test effect of fluoride on assay output in the presence of Cas13a without RNA polymerase in accordance with certain embodiments of the present disclosure.
FIG. 6B illustrates a schematic diagram of workflow for an exemplary two-batch assay used to measure effect of fluoride on RNA polymerase in accordance with certain embodiments of the present disclosure.
FIG. 6C represents an exemplary graph and histogram plot representing transcription mediated by RNA polymerase as measured by an exemplary two-batch assays in the presence of increasing concentrations of fluoride in accordance with certain embodiments of the present disclosure.
FIG. 6D represent exemplary a histogram plot of data obtained from exemplary assays to test effects of various agents on fluorescent signal emitted by assays in accordance with certain embodiments of the present disclosure.
FIG. 6E represent exemplary a histogram plot of data from an exemplary two batch assay to test effects of various agents on fluorescent signal emitted by an assay disclosed herein in accordance with certain embodiments of the present disclosure.
FIG. 6F illustrates structures of various agents used in certain assays in accordance with certain embodiments of the present disclosure.

The *B. cereus* crcB fluoride riboswitch is a regulatory switch that turns on expression of the fluoride efflux pump crcB via selectively binding fluoride over chloride. Using the SPRINT assay, a $T_{50}$ value of 11±1 μM was measured (FIG. 4C), which was lower than observed $K_D$ values of approximately 60 μM resulting from in-line probing. This may be explained in part by an observed inhibition of the assay at fluoride concentrations above 100 μM. To understand whether this effect stems from inhibition of the *E. coli* RNAP or inhibition of Cas13a, SHERLOCK reactions without RNAP were conducted at varying concentrations of sodium fluoride (FIG. 6A). Cas13a was gradually inhibited with increasing fluoride concentrations and the Cas13a activity sharply dropped around 600 μM. To measure the response of the RNAP to fluoride, an exemplary two-batch protocol was developed (FIG. 6B) to first transcribe RNA in presence of fluoride, then wash out the fluoride and add the washed transcripts to Cas13a. Fluoride induced transcription from the fluoride riboswitch in a linear manner up until concentrations of 100 μM, but at concentrations of 125 μM or above, NaF drastically reduced transcriptional activity (FIG. 6C). This suggested that the *E. coli* RNAP itself was the most fluoride-sensitive component in the SPRINT reactions. These data showed how the two-step assay was be used to separate in vitro transcription reactions from Cas13a reactions. The two-batch assay could also be used to wash out Cas13a-inhibiting compounds after transcription that would otherwise interfere with the assay.

The SELEX method (previously described) has been used to select the P1 aptamer that binds to the neurotransmitter serotonin (i.e. 5-hydroxytryptamine) and this aptamer was incorporated into the expression platform pbuE' to generate a riboswitch for serotonin. Surprisingly, serotonin specifically inhibited the transcription and also Cas13 reaction, whereas related agonists such as 5-hydroxytryptophan did not cause inhibitory effects (FIGS. 6D-6F). The $T_{50}$ value was measured as 5±3 μM for serotonin and the riboswitch discriminated specifically against tryptamine (FIG. 4D). Despite the idiosyncratic inhibition by serotonin, these exemplary results demonstrated how synthetically generated aptamers can be plugged into existing SPRINT platforms to create new sensors.

Example 4

Characterization of Various Expression Platforms with SPRINT

While the aptamer domain was mainly responsible for determining the affinity and specificity of ligand binding, the expression platform of a riboswitch largely determined stringency and dynamic range of the riboswitch, as well as the ON or OFF nature of the riboswitch. Therefore, further exemplary studies herein explored whether SPRINT could serve as a platform to detect subtle differences between expression platforms to facilitate the engineering of new riboswitches. The uracil-tract at the 3'-end of the pbuE* expression platform has previously been shown to affect in vitro transcription via the riboswitch. Therefore, variants of the xpt/pbuE* riboswitch with 5, 6, or 7 uracils in the tract were measured (FIG. 4E). Longer U-tracts following the intrinsic terminator led to a reduced transcriptional read-through in presence and absence of ligand. This demonstrated how a diversity of expression platforms could be screened for improved performance parameters, such as lower background activation.

Example 5

An Assay System Rapidly Assesses Native Riboswitch Function

Figures 7A, 7B, 7C, 7D:
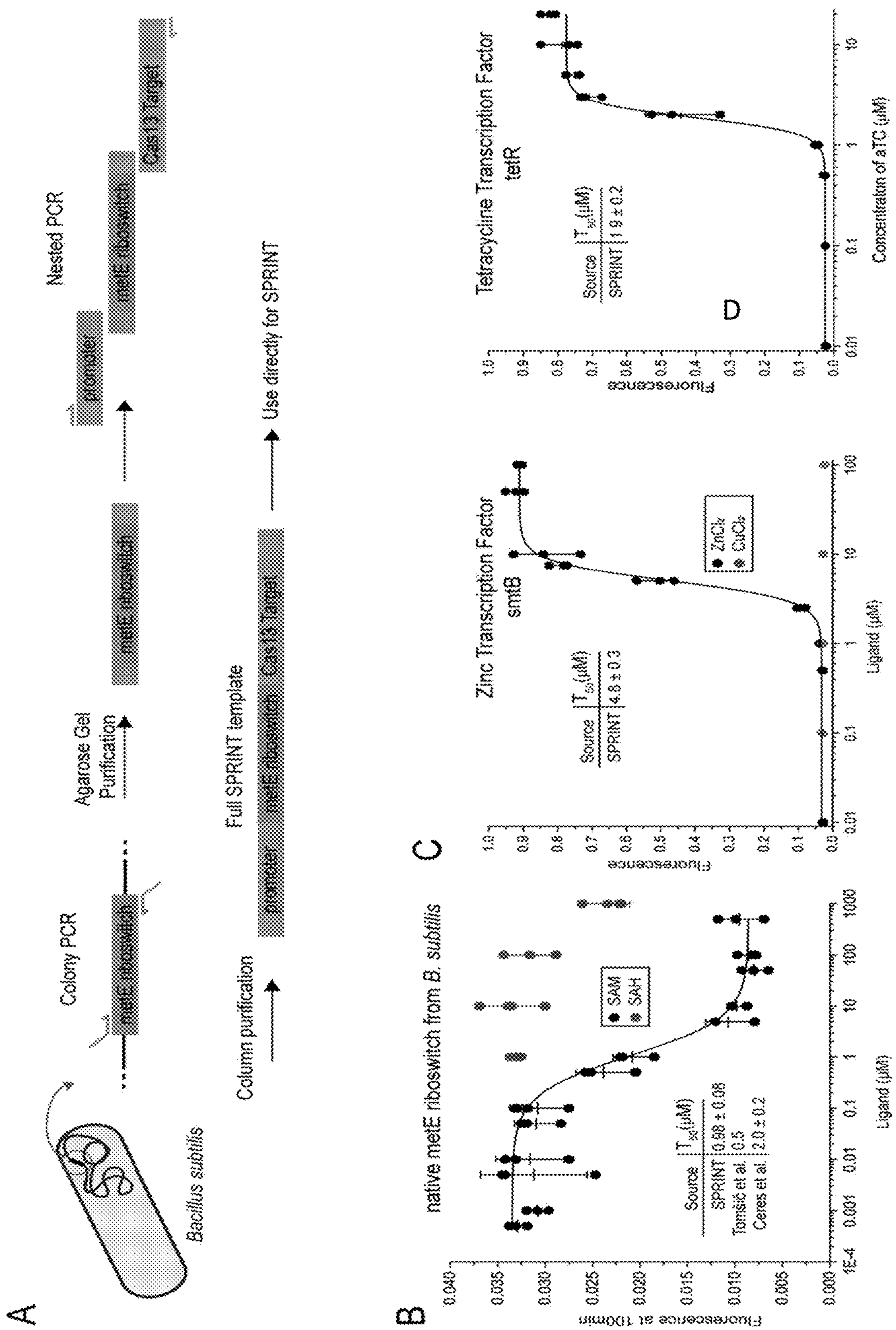
FIG. 7A illustrates a schematic diagram of a workflow for preparing a DNA template (e.g. SPRINT template) with a genomic riboswitch of use herein in accordance with certain embodiments of the present disclosure.
FIG. 7B illustrate exemplary graph representing data from an exemplary assay used to measure concentrations of agents, with novel double stranded DNA sequences containing a metE "OFF" riboswitch in accordance with certain embodiments of the present disclosure.
FIG. 7C illustrate exemplary graph representing data from an exemplary assay used to measure concentrations of agents, with novel double stranded DNA sequences containing zinc-responsive transcription factor in accordance with certain embodiments of the present disclosure.
FIG. 7D illustrate exemplary graph representing data from an exemplary assay used to measure concentrations of agents with double stranded DNA sequences containing tetracycline-responsive transcription factor in accordance with certain embodiments of the present disclosure.
Figure 8:
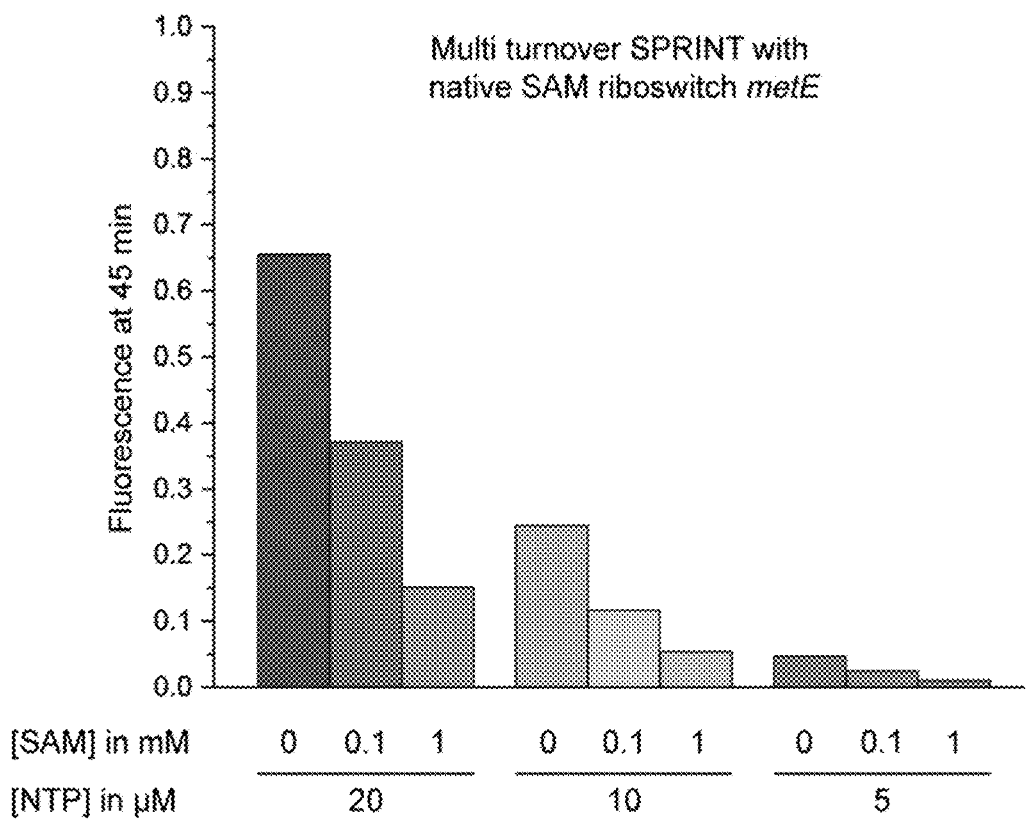
FIG. 8 represents a histogram plot of data from exemplary assays demonstrating transcription activity in the presence of an "OFF" riboswitch with increasing concentrations of an exemplary inhibitor in accordance with certain embodiments of the present disclosure.

In another exemplary method, certain riboswitches described herein were re-engineered for certain properties such as wide dynamic range and a ligand-induced "ON". It was contemplated that any riboswitch can be used in methods, constructs and systems disclosed herein to test multiple agents for purposes sought. In this example, a metE riboswitch, an "OFF" switch from *B. subtilis* that responds to the metabolite SAM and stalls transcription when bound to its ligand was created and systems disclosed herein were tested. The native riboswitch sequence was amplified from the *B. subtilis* genome via colony PCR and, in another PCR step, added the tac promoter to the 5'-end and the Cas13a target transcript to the 3'-end of the riboswitch (FIG. 7A). The resulting PCR reaction product was then used directly as DNA template for SPRINT (FIG. 7B). Titration of SAM reduced the transcriptional rate with a $T_{50}$ value of around 1 μM which was similar to the previously established values of 0.5 and 2 μM. Initially, measurements at intermediate concentrations of SAM were difficult to quantify because the high rate of transcription from the *B. subtilis* metE OFF-switch required very high concentrations of SAM to repress the signal (FIG. 8). To circumvent this issue, heparin was added to the SPRINT assay to restrict the RNA polymerase to a single turnover of transcription. Although the reaction was slowed down, the sensitivity of the assay was greatly improved.

Example 6

An Assay System Sensed Small Molecules via Transcriptional Repressor Protein

In another exemplary method, bacterial transcription can be regulated by allosteric transcription factors (aTFs), such as activators or repressors, which have previously been used for small molecule detection. Another system ("ROSALIND") enabled rapid detection of compounds via aTFs. In these reactions, transcription by the T7 RNA polymerase was blocked by an aTF that binds to an operator sequence downstream of the promoter (FIG. 1B). Ligand binding to the aTF led to de-repression and transcription of a broccoli-aptamer that binds to DFHBI-1T and increases its fluorescence. In this manner, 16 different compounds, including tetracyclines, macrolides, small molecules and metals were detected. The ROSALIND buffer system differs from the SPRINT or SHERLOCK buffer. Therefore, it was tested whether aTF-based ROSALIND reactions could be integrated with the Cas13a-based detection method. To simplify the system, the inorganic pyrophosphatase (IPPase) enzyme was first removed from the ROSALIND system. IPPase was used in transcription reactions to degrade pyrophosphate which was a reaction product of the RNA polymerase and can inhibit the reaction. However, as only picomolar concentrations of RNA triggered the Cas13a reaction, the production of pyrophosphate was expected to be negligible. Adaptions included reducing the concentrations of rNTP from 2.85 mM to 40 μM, DNA template from 25 to 15 nM, and T7 RNAP from 10 to 6.7 ng/μL.

The responses of the de-repressors tetR and smtB were measured with SPRINT. The de-repressor smtB enabled transcription in a zinc-dependent manner with a $T_{50}$ of 4.8±0.3 μM and demonstrated a high selectivity versus a control, copper (FIG. 7C). The repressor tetR responded to increasing concentrations of anhydrotetracycline with a $T_{50}$ of 1.9±0.2 μM, which was within the range of 1-2.5 μM previously reported. Surprisingly, these data demonstrated that SPRINT can not only measure regulation of *E. coli* RNAP by riboswitches, but also regulation of T7 RNAP by transcription factors. Combining these two mechanisms of detecting ligands expanded the scope of molecules that could be detected with the novel system SPRINT.

Example 7

Using the Assay System to Screen Exemplary Compounds

In another exemplary method, SPRINT assay systems disclosed herein were used because they provide a target-based yet functional platform for screening compounds against riboswitches because instead of binding, the actual transcriptional response of the riboswitch was measured in a completely defined in vitro system. This is one important observation, given that many riboswitches rely on the kinetics of co-transcriptional ligand binding as opposed to binding at equilibrium.

Figures 9A, 9B, 9C, 9D, 9E, 9F:
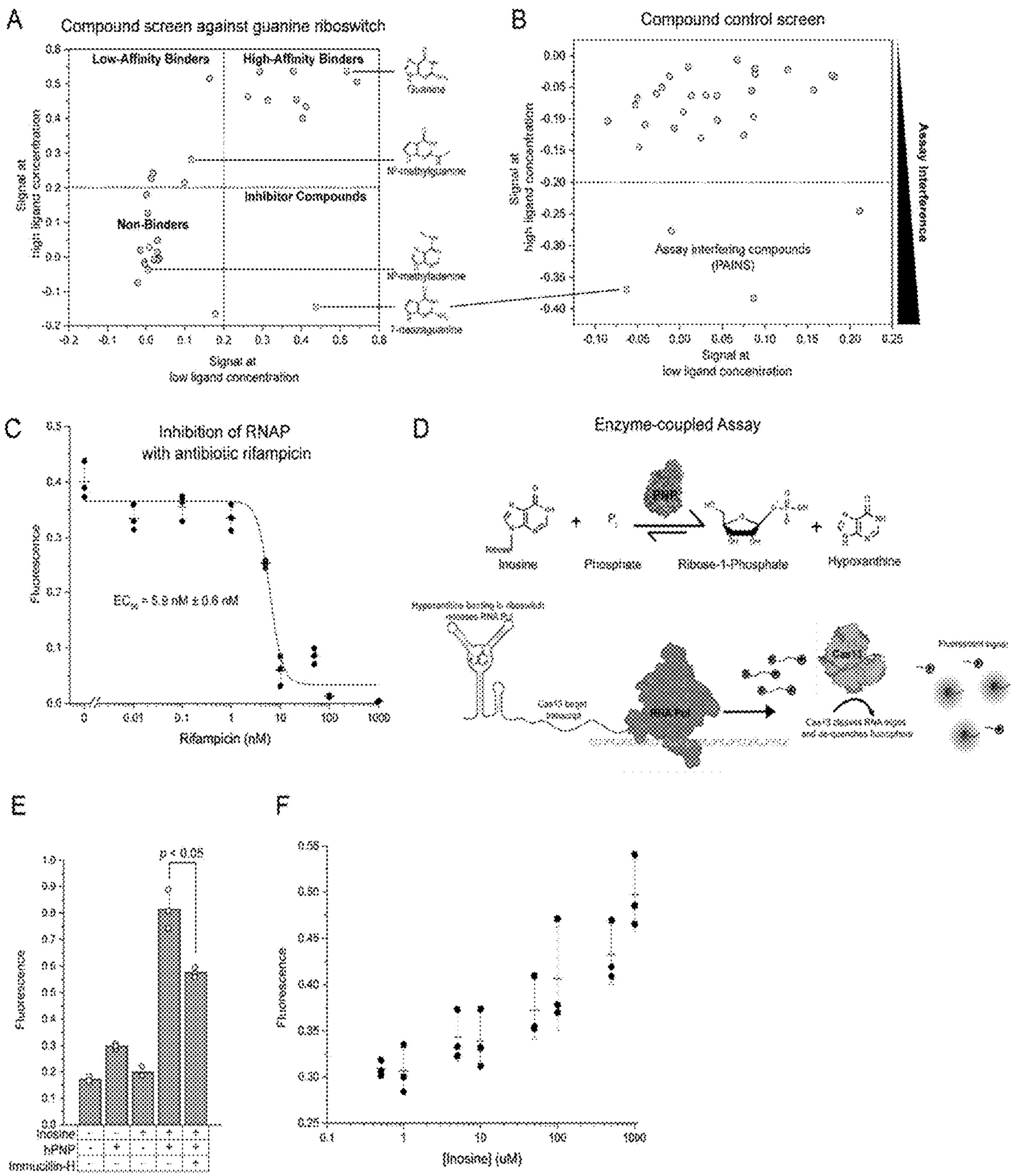
FIG. 9A represents plots of data from an exemplary screening test of compounds where each compound binding activity was assessed as a phenotypic output measured by transcriptional response to the compound binding to the guanine riboswitch upstream of a Cas13a target sequence, in accordance with certain embodiments of the present disclosure.
FIG. 9B represents plots of data from an exemplary screening test of compounds used in FIG. 9A where the compound binding activity was assessed as a phenotypic output measured by transcriptional response in the presence of a constitutively active promoter upstream of a Cas13a target sequence to identify pan-assay interference compounds (PAINS) in accordance with certain embodiments of the present disclosure.
FIG. 9C represents an exemplary graph depicting a decrease in measured fluorescence with increasing concentrations of rifampicin which is representative of attenuated transcriptional activity of an endogenous promoter upstream of a Cas13a target sequence in accordance with certain embodiments of the present disclosure.
FIG. 9D is a schematic diagram depicting a mechanism of an enzyme-coupled assay used to measure the enzymatic activity by the hPNP enzyme by quantifying conversion of inosine to hypoxanthine via hPNP using the guanine riboswitch xpt/pbuE*6U upstream of a Cas13a target sequence in accordance with certain embodiments of the present disclosure.
FIG. 9E represents an exemplary histogram plot depicting substrate-dependent increase of hPNP enzyme activity, in the presence or absence of an inhibitor, as measured by observed fluorescence resulting from increased transcriptional output of the guanine riboswitch in accordance with certain embodiments of the present disclosure.
FIG. 9F is an exemplary plot depicting concentration-dependent increase of hypoxanthine production by the hPNP enzyme in the presence of increasing concentrations of inosine as measured by observed fluorescence resulting from decreased transcriptional output of the guanine riboswitch in accordance with certain embodiments of the present disclosure.
Figure 10:
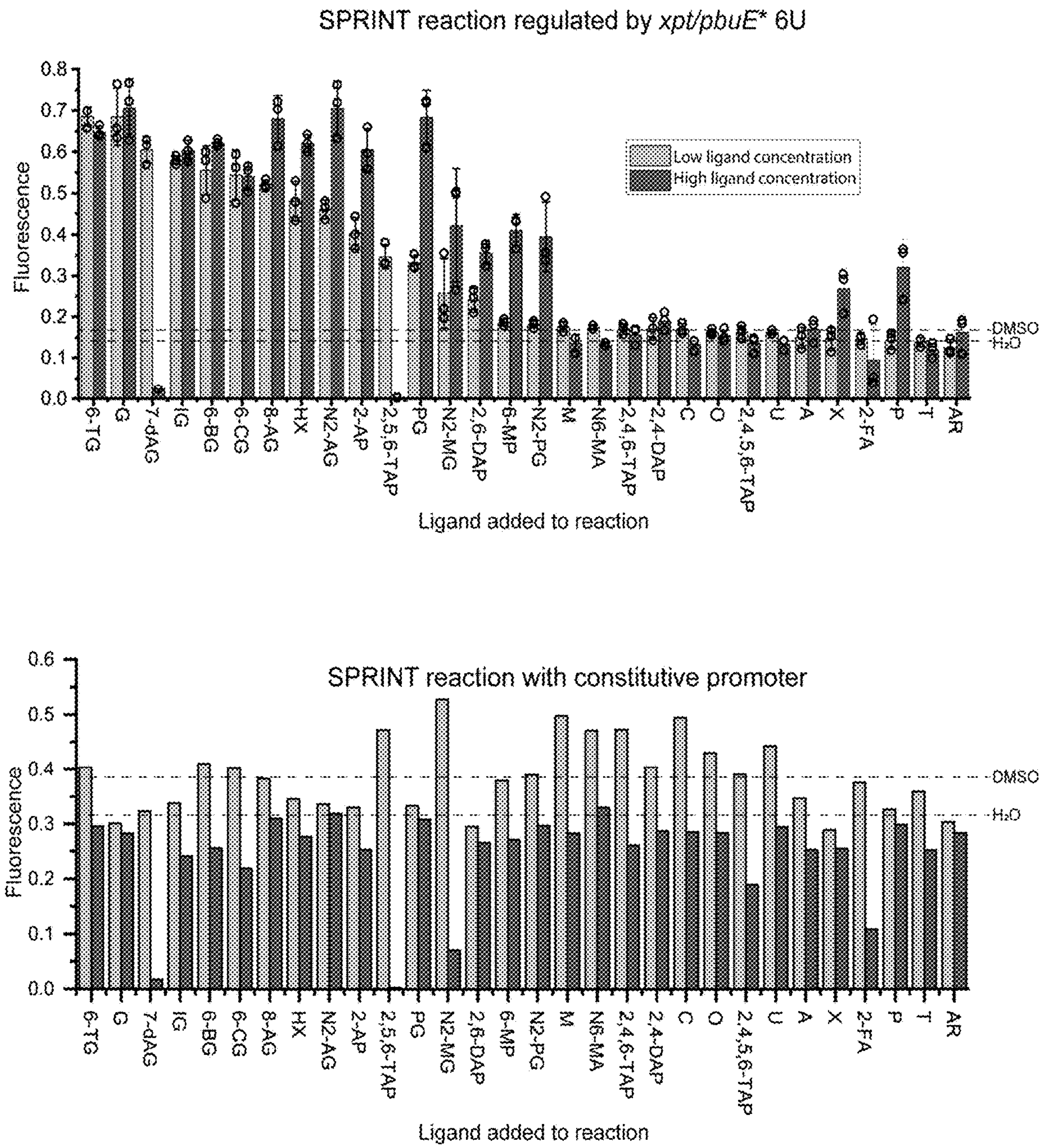
FIG. 10 represent exemplary histogram plots from an exemplary screen of compounds for their effect on a guanine riboswitch as measured using novel double stranded DNA sequences in accordance with certain embodiments of the present disclosure.

Briefly, the transcriptional response of the guanine riboswitch xpt/pbuE*6U to 30 different compounds was measured at two different concentrations each (FIG. 9A and FIG. 10). The concentrations used were 10 μM and 1 mM for most compounds. The signal that was obtained from control experiments with the solvents DMSO or water was subtracted from all values. Compounds such as guanine that elicited an equally strong transcriptional activation at low and high concentrations were found in the upper right quadrant of a graph of signal at high concentration versus signal at low concentration (FIG. 9A) and could be classified as efficient activators of transcription. Compounds such as N2-methylguanine that only caused a strong transcriptional response at high concentrations were found in the upper left quadrant and were expected to be low-affinity binders. Compounds such as N6-methyladenine that did not cause a transcriptional response at low or high concentrations were in the lower left quadrant. Compounds such as 7-deazaguanine that demonstrated some activation of transcription at low concentrations but no or reduced activation at high concentrations were suspected to inhibit transcription at higher concentrations.

To control for effects that those compounds have on the assay itself, the panel was also tested in SPRINT reactions with DNA templates that do not encode a riboswitch but instead constitutively transcribe a Cas13a target from the same promoter (FIG. 9B). These measurements were not affected by any specific interactions between ligand and RNA molecule. Therefore, the inhibitory effect that any compound has on the SPRINT assay could be quantified to identify pan-assay interference compounds (PAINS). In this way, compounds such as 7-deazaguanine, N2-methylguanine, 2,5,6-triaminpyrimidin-4-one (2,5,6-TAP) and to a lesser extent 2-fluoroadenine were identified as interfering compounds. Interestingly, 2,5,6-TAP was previously described as having bactericidal properties at concentrations of 8 mM and this antibiotic property was ascribed to its ability to bind the guanine riboswitch at concentrations as low as 100 nM. In the SPRINT screen, 2,5,6-TAP only slightly activated transcription at 1 μM but at 100 μM completely shut down enzymatic activity of the SPRINT assay (FIG. 9B, FIG. 10). This suggested that the antibiotic activity of 2,5,6-TAP might not have been caused by binding to the riboswitch but rather to other targets in the cell.

Several studies were directly aimed at identifying novel antibiotics by targeting the transcriptional machinery of bacteria. This can include targeting riboswitches, transcription factors, or the RNA polymerase itself. Rifampicin inhibited the bacterial RNAP by blocking elongation and was the leading drug to treat mycobacterial infections such as tuberculosis. It was tested how far the inhibitory effect of rifampicin on the RNAP could be measured with SPRINT. A transcription reaction with a constitutive promoter was titrated with different concentrations of rifampicin (FIG. 9C). A $T_{50}$ value of 5.9±0.6 nM was obtained, which was close to the established $K_D$ of 3 nM.

Together, these results demonstrated how the SPRINT platform can rapidly characterize compounds that targeted different aspects of the transcriptional machinery such as riboswitches or polymerases in target-based manner. Furthermore, by screening for actual transcription output and not binding affinity, a screening platform was designed with improved biological relevance over binding assays. This approach could also facilitate the identification of ligands for "orphan" riboswitches that may not be associated with any known ligands yet.

Example 8

Enzyme-Coupled Assay

In another exemplary method, as used herein, activity of an enzyme can be determined by monitoring substrate depletion or product generation indicating enzymatic activity and/or level of enzymatic activity. However, substrate or product are often undetectable using methods such as fluorescence spectroscopy due to below detection levels or inability to distinguish by observation of fluorescent output. To address this issue, enzyme-coupled assays can be used to convert substrate or product of a reaction into an easily detectable compound. However, these assays are often focused on the detection of one particular metabolite, such as ADP generated in a kinase reaction or NADH generated in a redox reaction. Detecting components of an enzymatic reaction with a riboswitch or transcription factor is an attractive alternative, because of the large diversity of compounds that can be detected with these systems, such as metal ions, nucleotides, amino acids, etc.

As part of the human purine metabolism, the enzyme purine nucleoside phosphorylase (hPNP) can catalyze the phosphorylation of the ribose moiety of various purines and thereby remove the sugar from the nucleobase. The conversion of deoxyguanosine to deoxyguanine by hPNP can be inhibited with nucleoside analogs such as Immucillin-H (forodesine) which leads to accumulation of deoxyguanosine and consequent apoptosis in activated T-cells. Therefore, hPNP is an important drug target for the treatment for example, of leukemia, arthritis, multiple sclerosis and transplant rejection.

In these systems, the conversion of inosine to hypoxanthine via hPNP was coupled to the SPRINT reaction in a one-batch buffer system using the guanine riboswitch xpt/pbuE*6U (FIG. 9D). The guanine riboswitch can detect hypoxanthine but does not bind nucleosides. This enzyme-coupled assay enabled the observation of enzymatic activity by the hPNP enzyme (FIG. 9E). Adding Immucillin-H at 100-fold lower concentrations than the substrate inosine caused a significant reduction in the enzymatic activity as measured in the SPRINT assay (FIG. 9E). Also, a titration with inosine demonstrated a concentration-dependent increase of hypoxanthine production by the hPNP enzyme (FIG. 9F).

These exemplary methods demonstrated how SPRINT can be used to assess the activity of enzymes and measure the inhibition of such enzymes with drugs for designer drug assessment. Furthermore, the use of coupled enzymes allowed for the detection of substances that are as of yet undetectable by SPRINT. Inosine is not bound directly by any riboswitches or transcription factors, but the conversion of inosine to hypoxanthine enabled the detection of inosine in samples by a secondary detection method for assessment of inosine levels.

Example 9

Portable Assay Formats

Figure 11:
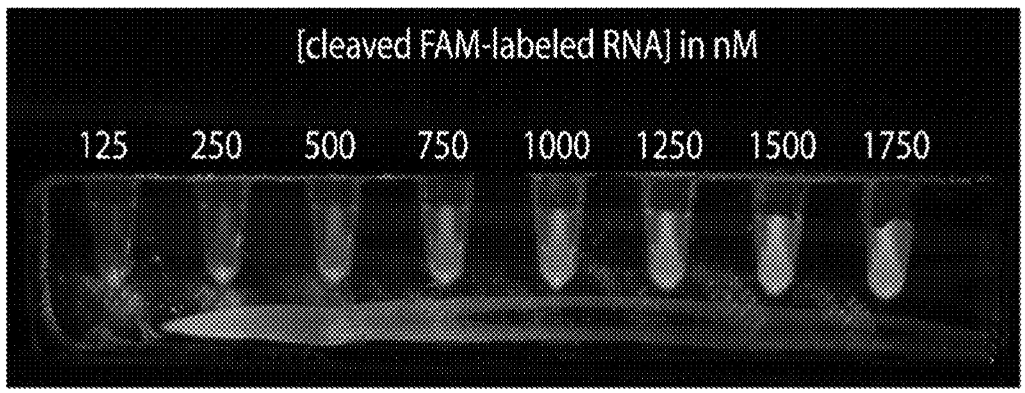
FIG. 11 illustrates exemplary images of fluorescently labeled RNA oligos in an illuminator device in accordance with certain embodiments of the present disclosure.

In other exemplary methods, to address the need for point-of-care diagnostic devices, in various exemplary methods, portable systems such as lateral flow assays (LFA) or portable fluorescent detections assays were developed. In order to convert assays disclosed herein such as SPRINT into an on-site detection system, it was adapted to a handheld device. This portable device illuminated the reaction tubes with blue light around 470 nm. The fluorescent probes could then be seen through a yellow plastic film that acts as a filter in this example. The concentration of FAM-labeled RNA was increased to 12.5 μM to make the fluorescence easily visible to the human eye (FIG. 11). Using the fluoride riboswitch, different fluoride concentrations were differentiated by eye after 20 minutes of reaction time (FIG. 12A) at 30° C. which was easily achieved by tightly holding the tubes in the hand.

Figures 12A, 12B:
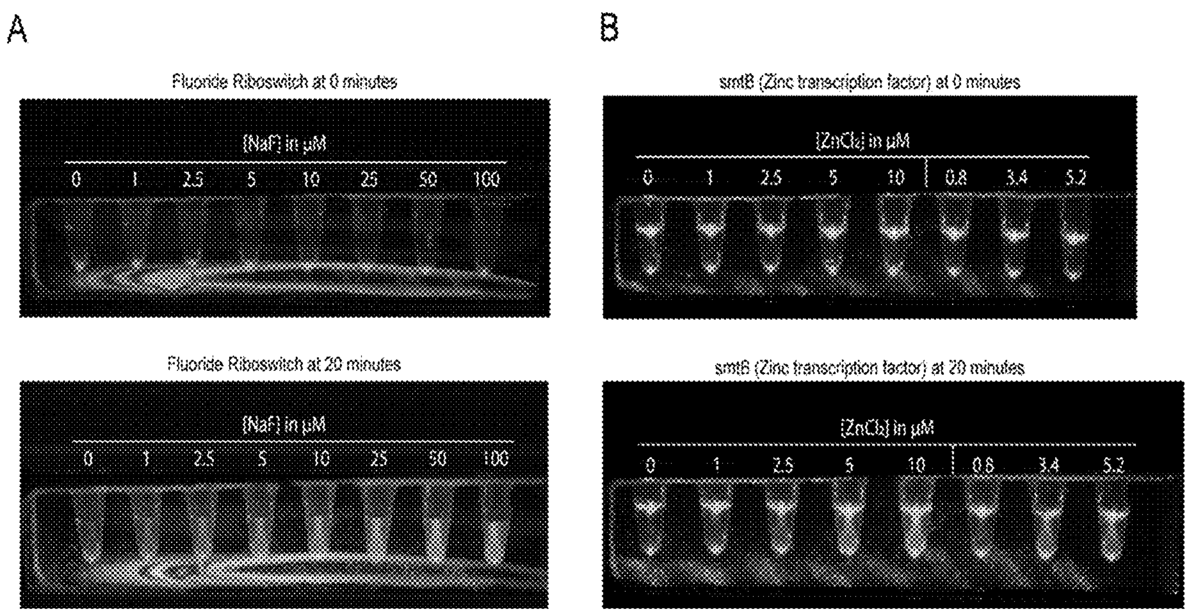
FIGS. 12A and 12B illustrate exemplary images of fluorescently labeled RNA oligos generated in different reaction conditions in a handheld detector in accordance with certain embodiments of the present disclosure.

Further, the zinc-responsive transcription factor smtB was used to detect zinc in environmental water samples with the illuminator device (FIG. 12B). By comparing the fluorescence of the environmental samples with the calibration curve, the zinc concentration of the samples from left to right was approximated by eye to be around 0-1 μM, 2.5-5 μM and around 5 μM, respectively. The concentration of zinc that was displayed for the environmental samples was previously determined by a cumbersome flame atomic absorption spectroscopy (FAAS) method. These exemplary methods demonstrated that the assay was not inhibited by trace elements in environmental water and can therefore be used for field testing.

The foregoing discussion of the disclosure has been presented for purposes of illustration and description. The foregoing is not intended to limit the disclosure to the form or forms disclosed herein. Although the description of the disclosure has included description of one or more embodiments and certain variations and modifications, other variations and modifications are within the scope of the disclosure, e.g., as can be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A system for quantifying transcriptional output in a sample, the system comprising:

at least one type VI CRISPR-Cas effector protein capable of binding a guide RNA;

at least one guide RNA (crRNA);

at least one double-stranded DNA sequence, wherein the at least one double-stranded DNA sequence comprises at least one transcriptional promoter, at least one regulatory element, and at least one target sequence;

at least one fluorescently labeled RNA oligonucleotide comprising a non-target sequence; and, at least one RNA polymerase;

wherein the at least one type VI CRISPR-Cas effector protein exhibits collateral RNase activity and cleaves the non-target sequence of the at least one fluorescently labeled RNA oligonucleotide after the at least one type VI CRISPR-Cas effector protein associates with the crRNA and a transcribed target RNA sequence, and wherein the at least one double-stranded DNA sequence comprises a polynucleotide having at least 85% sequence homology to any one of the polynucleotides represented by SEQ ID NOs: 36-45.

2. The system according to claim 1, further comprising at least one of: wherein the at least one type VI CRISPR-Cas effector protein comprises a Cas13 orthologue; wherein the at least one regulatory element comprises at least one riboswitch sequence; and wherein the at least one regulatory element comprises at least one allosteric transcription factor (aTF) operator sequence.

3. The system according to claim 1, wherein the system is configured to measure transcription of the at least one target sequence based on presence, absence, or level of emission of a fluorescent signal by the at least one fluorescently labeled RNA oligonucleotide comprising the non-target sequence.

4. The system according to claim 1, wherein the system is configured to detect at least one analyte or a target molecule that modulates transcription.

5. The system according to claim 1, wherein the system is configured to detect at least one of absence, presence and concentration of an analyte or a target molecule in the sample.

6. The system according to claim 1, wherein the at least one target sequence comprises a target polynucleotide of about 20 or more polynucleotides in length.

7. The system according to claim 1, wherein the sample comprises a sample from a subject.

8. The system according to claim 7, wherein the sample from a subject comprises a blood, serum, urine, tear, plasma, saliva, skin, tissue, other body fluid or other sample from a subject.

9. The system according to claim 1, wherein the sample comprises an environmental sample.

10. The system according to claim 9, wherein the environmental sample comprises a soil, air, water, sewage, sediment, oil, drainage, or other environmental sample.

11. A method for quantifying transcriptional output in a sample comprising:

(a) contacting one or more samples with:

a composition comprising;

at least one type VI CRISPR-Cas effector protein;

at least one guide RNA (crRNA);

at least one double-stranded DNA sequence, wherein the at least one double-stranded DNA sequence comprises a transcriptional promoter, at least one regulatory element, and at least one target sequence;

at least one fluorescently labeled RNA oligonucleotide comprising a non-target sequence; and, at least one RNA polymerase;

wherein the at least one type VI CRISPR-Cas effector protein exhibits collateral RNase activity and cleaves the non-target sequence of the at least one fluorescently labeled RNA oligonucleotide after the at least one type VI CRISPR-Cas effector protein associates with the crRNA and a transcribed target RNA sequence, and wherein the at least one double-stranded DNA sequence comprises a polynucleotide having at least 85% sequence homology to any one of the polynucleotides represented by SEQ ID NOs: 36-45; and (b) detecting a signal from cleavage of the non-target sequence, and optionally, measuring at least one of presence, absence and intensity of the signal and quantifying transcriptional output in the one or more samples.

12. The method according to claim 11, comprising at least one of:

wherein the at least one type VI CRISPR-Cas effector protein comprises a Cas13 orthologue;

wherein the at least one regulatory element comprises at least one riboswitch sequence; and wherein the at least one regulatory element comprises at least one allosteric transcription factor (aTF) operator sequence.

13. The method according to claim 11, wherein the method quantitates level of one or more of an enzyme activity, compound or agent that modulates transcription, concentration of an agent, concentration or presence of a pathogen, concentration of a contaminant, concentration of a monatomic ion, concentration of a supplement or concentration of other comparable substance.

14. The method according to claim 11, wherein the at least one guide RNA (crRNA) comprises a polynucleotide having at least 85% sequence homology to the polynucleotide represented by SEQ ID NO. 18.

* * * * *